United States Patent [19]

Carson et al.

[11] Patent Number: 4,937,373

[45] Date of Patent: Jun. 26, 1990

[54] SUBSTITUTED NAPHTHALENE CARBOXYLIC ACIDS

[75] Inventors: Matthew Carson, Nutley; Ru-Jen L. Han, Princeton; Ronald A. LeMahieu, North Caldwell, all of N.J.

[73] Assignee: Hoffmann-La Roche Inc., Nutley, N.J.

[21] Appl. No.: 282,100

[22] Filed: Dec. 8, 1988

[51] Int. Cl.$^5$ .............................................. C07C 69/76
[52] U.S. Cl. ..................... 560/056; 562/466; 562/463; 560/53
[58] Field of Search ............... 560/56, 53; 562/463, 562/466; 514/545, 532, 569

[56] References Cited

U.S. PATENT DOCUMENTS 4,622,419 11/1986 Cannata et al. .................... 560/56

FOREIGN PATENT DOCUMENTS

87/06577 11/1987 PCT Int'l Appl. ................... 560/56

*Primary Examiner*—Paul J. Killos
*Attorney, Agent, or Firm*—George M. Gould; Bernard S. Leon; William G. Isgro

[57] ABSTRACT

The invention relates to substituted naphthalene carboxylic acid derivatives of the formula

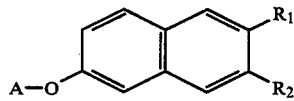

wherein one of $R_1$ and $R_2$ is

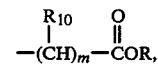

and the other is hydrogen, wherein R is hydrogen or lower alkyl, $R_{10}$ is hydrogen or lower alkyl, and m is 0 or 1 A is

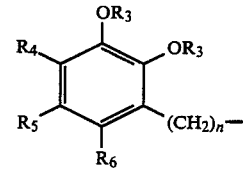

wherein $R_3$ is hydrogen or acyl, $R_4$ is a hydrogen, halogen, lower alkyl, aryl or cycloalkyl, $R_5$ and $R_6$ independently are hydrogen or halogen, and n is an integer from 2–10, or A is

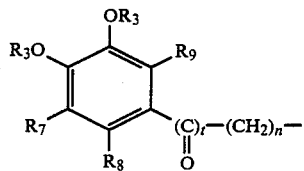

wherein $R_3$ is hydrogen or acyl, $R_7$ is hydrogen or lower alkyl, $R_8$ and $R_9$, independently, are hydrogen, lower alkyl or halogen, t is 0 or 1, and n is an integer from 2–10, and, when $R_{10}$ is lower alkyl, enantiomers and racemates thereof, and, when R is hydrogen, salts thereof with pharmaceutically acceptable bases.

29 Claims, No Drawings

SUBSTITUTED NAPHTHALENE CARBOXYLIC ACIDS

Brief Description of the Invention

The invention relates to substituted naphthalene carboxylic acid derivatives of the formula

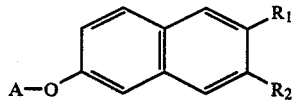

I wherein one of $R_1$ and $R_2$ is

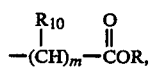

and the other is hydrogen, wherein R is hydrogen or lower alkyl, $R_{10}$ is hydrogen or lower alkyl, and m is 0 or 1, A is

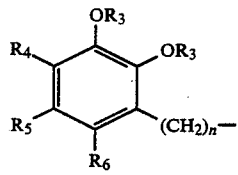

A' wherein $R_3$ is hydrogen or acyl, $R_4$ is hydrogen, halogen, lower alkyl, aryl or cycloalkyl, $R_5$ and $R_6$ independently are hydrogen or halogen, and n is an integer from 2–10, or A is

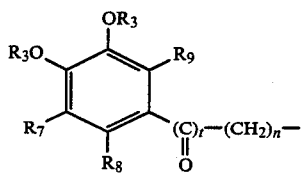

A'' wherein $R_3$ is hydrogen or acyl, $R_7$ is hydrogen or lower alkyl, $R_8$ and $R_9$, independently, are hydrogen, lower alkyl or halogen, t is 0 or 1, and n is an integer from 2–10.
and, when $R_{10}$ is lower alkyl, enantiomers and racemates thereof, and, when R is hydrogen, salts thereof with pharmaceutically acceptable bases.

The compounds of formula I are useful as agents for the treatment of inflammatory diseases such as arthritis, inflammatory bowel diseases such as colitis, skin diseases such as psoriasis by topical administration, and bronchopulmonary diseases such as asthma.

Detailed Description of the Invention

As used herein, the term "lower alkyl" denotes a straight or branched chain saturated hydrocarbon containing 1 to 7 carbon atoms, for example, methyl, ethyl, propyl, isopropyl, butyl t-butyl neopentyl, pentyl heptyl, and the like. Branched chain saturated hydrocarbons are preferred for $R_4$, and $R_7$. The term "halogen" denotes all the halogens, that is, bromine, chlorine, fluorine, and iodine. The term "aryl" denotes phenyl or phenyl bearing one or two substituents independently selected from the group consisting of halogen, trifluoromethyl, lower alkyl, lower alkoxy, nitro, amino, lower alkylamino and di-lower alkylamino. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, for example, benzoyl and the like. The term "cycloalkyl" denotes preferably a cyclic hydrocarbon of 3 to 6 carbon atoms which may be unsubstituted or substituted by lower alkyl and most preferably of 5 to 6 carbon atoms, for example, cyclopropyl, cylcopentyl, cyclohexyl or the like.

The invention relates to substituted naphthalene carboxylic acid derivatives of the formula

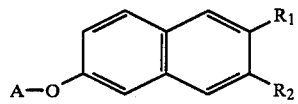

I wherein one of $R_1$ and $R_2$ is

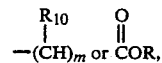

and the other is hydrogen, wherein R is hydrogen or lower alkyl, $R_{10}$ is hydrogen or lower alkyl, and m is 0 or 1, A is

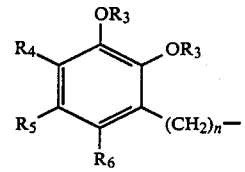

A' wherein $R_3$ is hydrogen or acyl, $R_4$ is hydrogen, halogen, lower alkyl, aryl or cycloalkyl, $R_5$ and $R_6$ independently are hydrogen or halogen, and n is an integer from 2–10, or A is

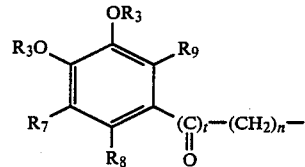

A'' wherein $R_3$ is hydrogen or acyl, $R_7$ is hydrogen or lower alkyl, $R_8$ and $R_9$, independently, are hydrogen, lower alkyl or halogen, t is 0 or 1, and n is an integer from 2–10, and, when $R_{10}$ is lower alkyl, enantiomers and racemates thereof, and, when R is hydrogen, salts thereof with pharmaceutically acceptable bases.

The compounds of formula I can also be characterized by the formulas Ia and Ib, depending upon whether the moiety A is fragment A' or A'', respectively, as follows:

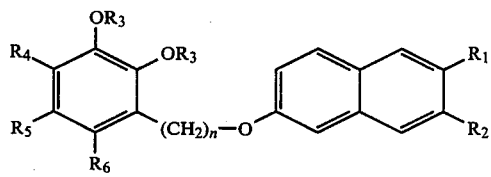

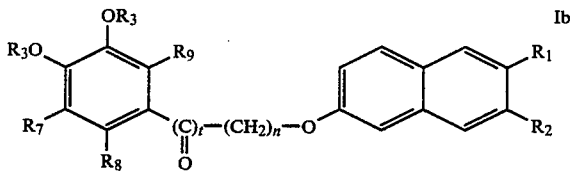

$R_1$, $R_2$, $R_3$, $R_4$, $R_5$, $R_6$, $R_7$, $R_8$, $R_9$, t and n are as herein described.

Preferred compounds of formula Ia of the invention are those wherein $R_1$ is

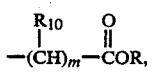

$R_2$ is hydrogen, $R_{10}$ is hydrogen or methyl, $R_3$ is hydrogen and R, $R_4$, $R_5$, $R_6$, m and n are as previously described.

Preferred compounds of formula Ib of the invention are those wherein $R_1$ is

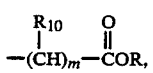

$R_{10}$ is hydrogen or methyl, $R_3$ is hydrogen and R, $R_7$, $R_8$, $R_9$, m, t and n are as previously described.

More preferred compounds of formula Ia are those wherein $R_1$ is

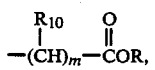

$R_2$ is hydrogen, $R_{10}$ is hydrogen, or methyl, $R_3$ is hydrogen, $R_4$ is hydrogen, halogen or lower alkyl n is an integer from 4 to 8, and R, $R_5$, $R_6$ and m are as previously described More preferred compounds of formula Ib are those wherein $R_1$ is

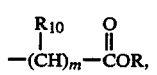

$R_2$ is hydrogen $R_{10}$ is hydrogen or methyl, $R_3$ is hydrogen, t is 0, n is an integer from 4–8, $R_7$ and $R_9$ are hydrogen or lower alkyl, $R_8$ is hydrogen, and R and m are as previously described.

The most preferred compounds of the invention are:
(S)-6-[6-(2,3-dihydroxyphenyl)hexyloxy]-alpha-methyl-2-naphthaleneacetic acid:
(S)-6-[6-(2,3-dihydroxyphenyl)hexyloxy]-alpha-methyl-2-naphthaleneacetic acid ethyl ester;
(Rac)-6-[6-(2,3-dihydroxyphenyl)hexyloxy]-alpha-methyl-2-naphthaleneacetic acid:
6-[6-(2 3-dihydroxyphenyl)hexyloxy]-2-naphthaleneacetic acid;
6-[6-(2,3-dihydroxyphenyl)hexyloxy]-2-naphthalenecarboxylic acid; and
(S)-6-[6-(3,4-dihydroxyphenyl)hexyloxy]-alpha-methyl-2-naphth aleneacetic acid.

Exemplary of other compounds of the invention are:
(S)-6-[4-(2,3-dihydroxyphenyl)butoxy]-alpha-methyl-2-naphthaleneacetic acid:
6-[4-(2,3-dihydroxyphenyl)butoxy]-2-naphthalenecarboxylic acid:
(R)-6-[6-(2,3-dihydroxyphenyl)hexyloxy]-alpha-methyl-2-naphthaleneacetic acid:
(rac)-6-[4-(2,3-dihydroxyphenyl)butoxy]-alpha-methyl-2-naphthaleneacetic acid:
6-[4-(2,3-dihydroxyphenyl)butoxy]-2-naphthalenecarboxylic acid ethyl ester
(S)-7-[6-(2,3-dihydroxyphenyl)hexyloxy]-alpha-methyl-2-naphthaleneacetic acid; .
7-[6-(2,3-dihydroxyphenyl)hexyloxy]-2-naphthalenecarboxylic acid:
(R)-7-[6-(2,3-dihydroxyphenyl)hexyloxy]-alpha-methyl-2-naphthaleneacetic acid
(S)-6-[8-(2,3-dihydroxyphenyl)octyloxy]-alpha-methyl-2-naphthaleneacetic acid;
(S)-6-[6-(2,3-diacetoxyphenyl)hexyloxy]-alpha-methyl-2-naphthaleneacetic acid;
(S)-6-[6-[2,3-dihydroxy-4-(1-methylethyl)phenyl]hexyloxy]-alpha-methyl-2-naphthaleneacetic acid;
(S)-6-[4-[2,3-dihydroxy-4-(1,1-dimethylethyl)phenyl]butoxy]-alpha-methyl-2-naphthaleneacetic acid;
(R)-6-[6-[2,3-dihydroxy-4-1-methylethyl)phenyl]hexyloxy]-alpha-methyl-2-naphthaleneacetic acid;
7-[4-(2,3-dihydroxyphenyl)butoxy]-2-naphthalenecarboxylic acid;
(S)-6-[5-(6-chloro-2,3-dihydroxyphenyl)pentyloxy]-alpha-methyl-2-naphthaleneacetic acid:
(S)-6-[5-(5,6-dichloro 2,3-dihydroxyphenyl)pentyloxy]-alpha-methyl-2-naphthaleneacetic acid;
(S)-6-[5-(2,3-dihydroxy-4,5,6-trichlorophenyl)pentyloxy]-alpha-methyl-2-naphthaleneacetic acid;
(S)-7-[5-(2,3-dihydroxy-4,5,6-trichlorophenyl)pentyloxy]-alpha-methyl-2-naphthaleneacetic acid;
6-[5-(2,3-dihydroxy-4,5,6-trichlorophenyl)pentyloxy]-2-naphthalene carboxylic acid;
(R)-6-[5-(2,3-dihydroxy-4,5,6-trichlorophenyl)pentyloxy]-alpha-methyl-2-naphthaleneacetic acid;
(S)-6-[8-(3,4-dihydroxyphenyl)octyloxy]-alpha-methyl-2-naphthaleneacetic acid:
(S)-6-[4-(3,4-dihydroxyphenyl)butoxy-alpha-methyl-2-naphthaleneacetic acid:
6-[4-(3,4-dihydroxyphenyl)butoxy]-2-naphthalenecarboxylic acid;
(R)-6-[6-(3,4-dihydroxyphenyl)hexyloxy]-alpha-methyl-2-naphthaleneacetic acid;
7-[4-(3 . 4-dihydroxyphenyl)butoxy]-2-naphthalenecarboxylic acid;
(S)-6-[[6-(3,4-dihydroxyphenyl)-6-oxohexyl]oxy]-alpha-methyl2-naphthaleneacetic acid;
6-[[4-(3,4-dihydroxyphenyl-4-oxobutyl]oxy]-2-naphthalenecarboxylic acid;
(S)-6-[6-(3,4-dihydroxy-2,5-dimethylphenyl)hexyloxy]-alpha- methyl-2-naphthaleneacetic acid;
7-[6-(6-(3,4-dihydroxy-2,5-dimethylphenyl)hexyloxy]-2-naphthalenecarboxylic acid;
6-[6-(3,4-dihydroxy-2,5-dimethylphenyl)hexyloxy]-2-naphthalen ecarboxylic acid;
6-[[6-(3,4-dihydroxy-2,5-dimethylphenyl)-6-oxohexyl]oxy]-2-naphthaleneacetic acid:

6-[4-(2,3-dihydroxyphenyl)butoxy]-2-naphthaleneacetic acid
6-[6-[3,4-dihydroxy-5-(1-methylethyl)phenyl]hexyloxy]-2-naphthaleneacetic acid;
6-[6-(3,4-dihydroxy-6-fluorophenyl)hexyloxy]-2-naphthaleneacetic acid:
6-[6-(2,3-dihydroxyphenyl)hexyloxy]-2-naphthaleneacetic acid ethyl ester:

The compounds of Formula I, and intermediates therefor, can be prepared as described in Reactions Schemes I to VIII.

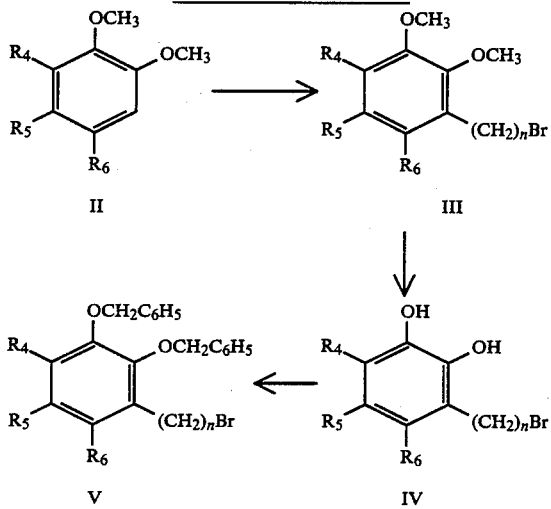

REACTION SCHEME I wherein $R_4$, $R_5$, $R_6$ and n are as previously described.

In Reaction Scheme I, a compound of formula II, which are known compounds or can be prepared according to known procedures, can be converted to the corresponding known compounds of formula III as described in H. Halim, H. D. Locksley and J. J. Memon, J. Chem. Soc. Perkin I, 2331 (1980). More particularly, a compound of formula II is reacted with an alkyl lithium reagent, preferably butyl lithium, in the presence of a solvent such as diethylether, tetrahydrofuran or the like at a temperature in the range of from about $-75°$ to $0°$, to yield the corresponding lithium salt followed by reaction in situ with an excess of a dibromo alkane at a temperature in the range of from about $0°$ to $50°$.

A compound of formula III can be converted to the corresponding compound of formula IV, for example, with boron tribromide in a halogenated hydrocarbon solvent, for example, chloroform or 1,2-dichloroethane or preferably methylene chloride at a temperature in the range of from about $-75°$ to about $25°$.

The resulting compound of formula IV can be converted to the corresponding compound of formula V in the presence of benzyl chloride, benzyl bromide or the like, potassium iodide or sodium iodide and an alkali metal carbonate, for example, sodium or potassium carbonate, in a solvent such as acetone, methyl ethyl ketone or the like, at reflux or with dimethyl formamide at a temperature in the range of from about $50°$ to about $100°$.

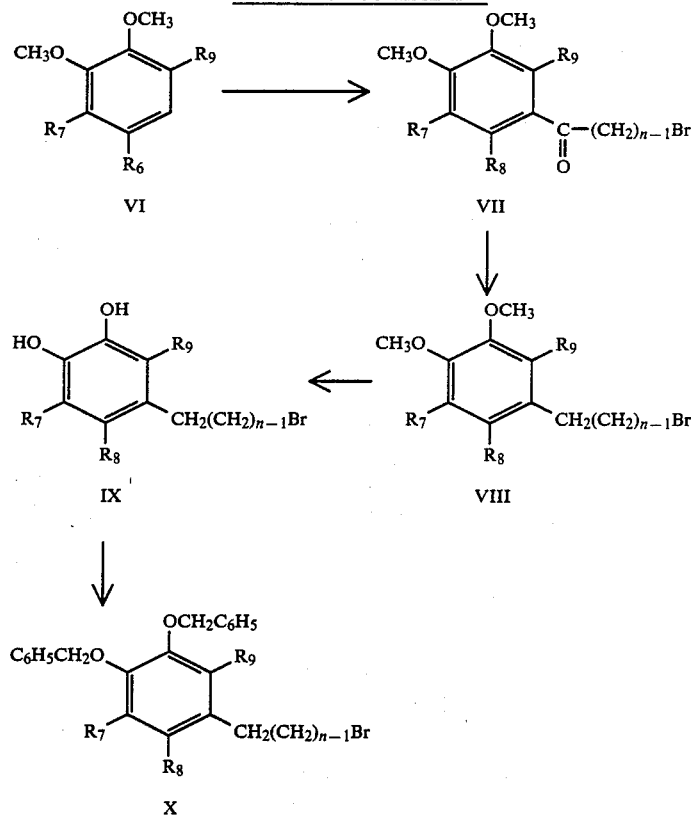

REACTION SCHEME II wherein $R_7$, $R_8$, $R_9$ and n are as previously described.

In Reaction Scheme II, a compound of formula VI, which are known compounds or can be prepared according to known procedures, can be converted to a compound of formula VII utilizing standard acylation conditions, for example, treatment with a bromo acid and trifluoroacetic anhydride at a temperature in the range of from 25° to about 40° without solvent or with a solvent such as methylene chloride, 1,2-dichloroethane or the like. Alternatively a bromoacid chloride and aluminum chloride in a solvent such as methylene chloride or 1,2-dichloroethane at a temperature in the range of from 0° to about 40° can also be utilized.

The reduction of a compound of formula VII to the corresponding compound of formula VIII can be accomplished by hydrogenation in a Parr apparatus at hydrogen pressures of about 50 to about 60 psi, using a palladium catalyst in a solvent such as ethanol, ethyl acetate, tetrahydrofuran or the like, at a temperature in the range of from 25° to about 70°. A mineral acid catalyst can be used in addition to palladium catalyst.

The conversion of a compound of formula VIII to a compound of formula IX and then to a compound of formula X can be carried out in a manner similar to that described in Scheme I for the conversion of III to IV and V.

REACTION SCHEME III

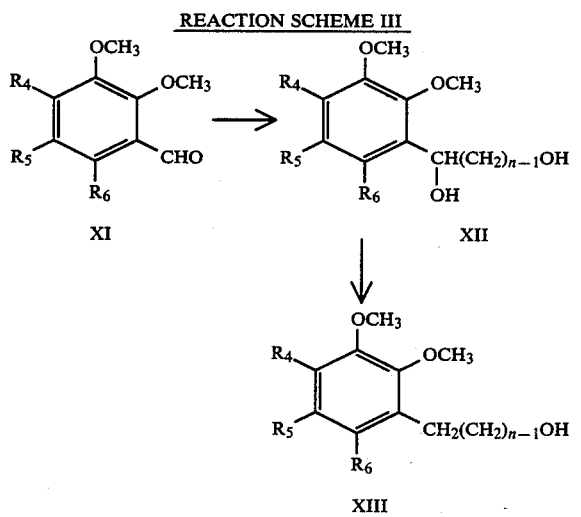

wherein $R_4$, $R_5$, $R_6$ and n are as previously described.

In Reaction Scheme III, an aldehyde of formula XI, which are known compounds or can be prepared according to known procedures, can be converted to the corresponding compound of formula XII as described in J. H. P. Tyman and C. H. Khor, Chem. Ind., 526 (1974). More particularly, the aldehyde of formula XI is allowed to react with a lithium reagent, prepared by standard procedures, in a solvent such as ethyl ether, tetrahydrofuran or the like, at a temperature in the range of from about −20° to about 35°. The alcohol protecting group can be removed from the product by treatment with dilute hydrochloric acid at 25° to give a diol of formula XII.

Thereafter, hydrogenolysis of a compound of formula XII gives the corresponding compound of formula XIII by shaking on a Parr apparatus under hydrogen pressure of from about 40–60 psi, using a palladium catalyst at a temperature in the range of from about 25 to about 50°, in a solvent, such as, ethyl acetate, ethanol, tetrahydrofuran and the like.

A compound of formula XIII can be converted to an intermediate of formula V, as described in Reaction Scheme I, that is, by treatment with boron tribromide followed by benzylation.

REACTION SCHEME IV

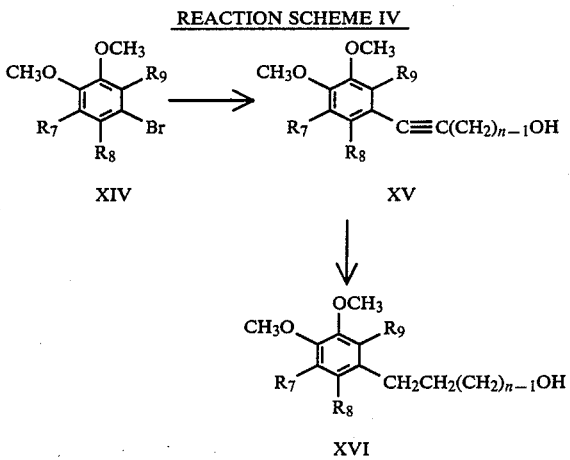

wherein $R_7$, $R_8$, $R_9$ and n are as previously described.

In Reaction Scheme IV, a compound of formula XIV is converted to an acetylenic alcohol of formula XV by reaction with an acetylenic alcohol in the presence of bis-(triphenylphosphine) palladium dichloride, cuprous iodide and an organic amine (triethylamine) as described in K. Sonogashira, Y. Tohda and N. Hagihara, Tet. Letters. 4467 (1975).

The reaction is carried out in a solvent, for example, a halogenated hydrocarbon, for example, methylene chloride, chloroform, 1,2-dichloroethane and the like, at a temperature in the range of from about 25° to about 50°.

A resulting compound of formula XV is converted to a compound of formula XVI utilizing standard conditions, for example, catalytic hydrogenation at atmospheric pressure and room temperature.

A compound of formula XVI can be converted to an intermediate of formula X, as described in Reaction Scheme I, that is, by treatment with boron tribromide followed by benzylation.

REACTION SCHEME V

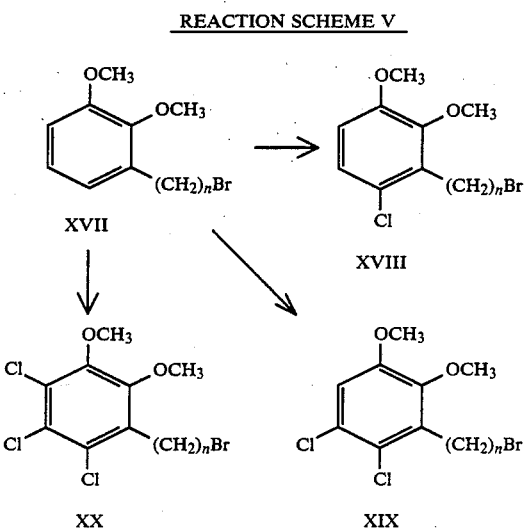

-continued
REACTION SCHEME V

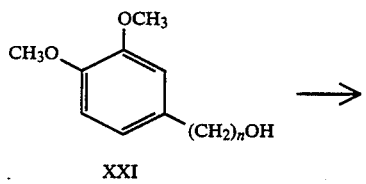

XXI

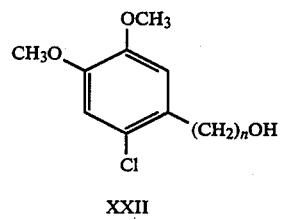

XXII wherein n is as previously described.

In Reaction Scheme V, a compound of formula XVII, which are known compounds or can be prepared according to known procedures, can be converted to the corresponding monochloro compounds of formula XVIII, the dichloro compounds of formula XIX and the trichloro compounds of formula XX by treatment with the appropriate quantity of chlorine, in an inert solvent such as a chlorinated hydrocarbon, for example, methylene chloride, chloroform, 1,2-dichloromethane and the like, at a temperature in the range of from about −20° to about 25°.

The conversion of a compound of formula XXI, which are known compounds or can be prepared according to known procedures, to the corresponding compound of formula XXII can be carried out utilizing the reaction condition first described above.

REACTION SCHEME VI

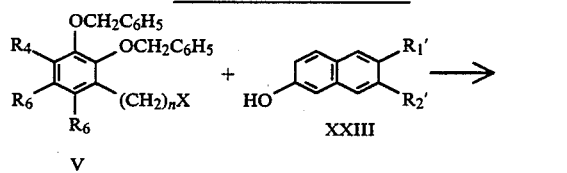

V

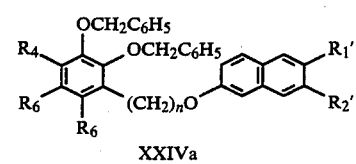

XXIVa

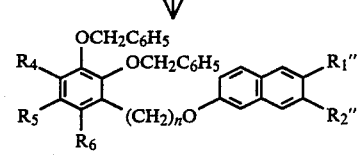

XXIVb

-continued
REACTION SCHEME VI

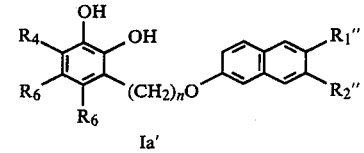

Ia' wherein X is halogen; one of $R_1'$ and $R_2'$ is hydrogen and the other is

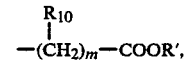

wherein R' is benzyl or lower alkyl, which includes the (R), (S) and (RS) configurations, when $R_{10}$ is lower alkyl; one of $R_1''$ and $R_2''$ is hydrogen and the other is

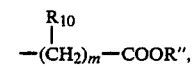

wherein R'' is hydrogen, which includes the (R), (S) and (RS) configurations when $R_{10}$ is lower alkyl; and $R_4$, $R_5$, $R_6$ and $R_{10}$ are as previously described.

In Reaction Scheme VI a compound of formula V is reacted with a compound of formula XXIII, which are known compounds or can be prepared according to known procedures, to yield the corresponding compound of formula XXIVa. The reaction is carried out utilizing an alkali metal carbonate as the base, for example, sodium carbonate, preferably potassium carbonate, with added sodium iodide or potassium iodide, in a solvent such as acetone, methyl ethyl ketone, dimethylformamide, toluene or the like, at a temperature in the range of from about 40° to about 70°. The solid-liquid phase-transfer catalyst tris[2-(2-methoxyethoxy)ethyl]amine can be used to facilitate the reaction when toluene is the solvent.

The hydrolysis of a compound of formula XXIVa to the corresponding compound of formula XXIVb can be carried out utilizing standard conditions, for example utilizing an alkali metal hydroxide such as sodium hydroxide or potassium hydroxide, in a solvent such as methanol, ethanol or the like, sometimes with added dioxane to aid solubility, at a temperature in the range of from about 25° to about 65°.

The conversion of a compound of formula XXIVb to the corresponding compound of formula Ia' can be carried out utilizing standard conditions for example, catalytic hydrogenation at atmospheric pressure and room temperature. The resulting compound of formula Ia' is recovered and purified utilizing known and conventional procedures, for example, precipitation, crystallization, chromatography or the like.

REACTION SCHEME VII

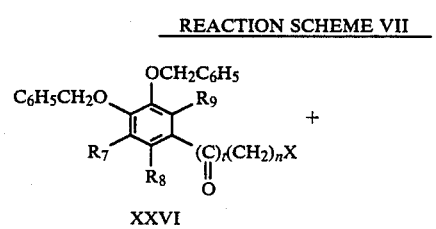

XXVI

-continued
REACTION SCHEME VII

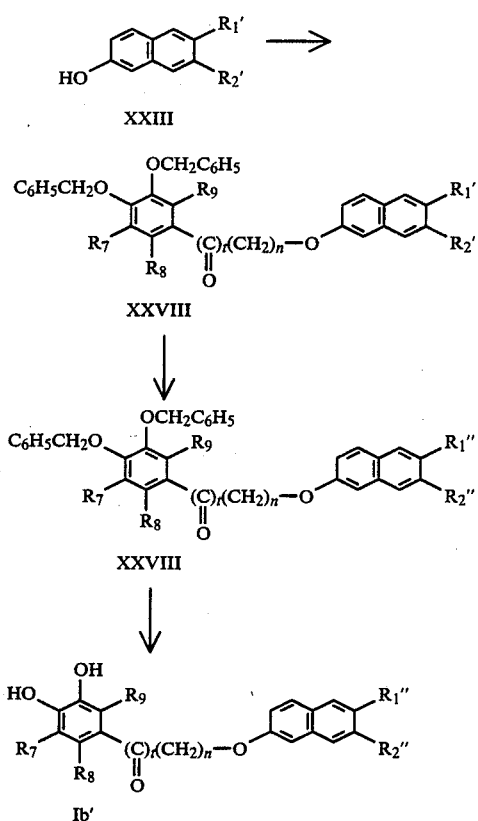

REACTION SCHEME VIII

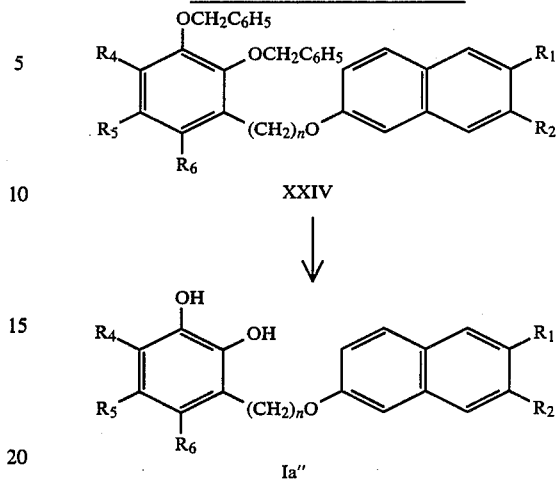

wherein $R_1$, $R_2$, $R_4$, $R_5$, $R_6$ and n are as previously described.

In Reaction Scheme VIII a compound of formula XXIV can be converted to a corresponding compound of formula Ia" by shaking in a hydrogen atmosphere at atmospheric pressure and room temperature in the presence of a catalyst such as palladium.

It is understood that preferably, but not necessarily, any intermediate prepared in Reaction Schemes I–VIII is recovered and isolated utilizing known procedures, for example, precipitation, crystallization, chromatography or the like, prior to use in the next reaction step. The end-products of formula I are recovered by similar known procedures.

The invention also relates to salts of the compound of formula I, when R is hydrogen, which salts are prepared by the reaction of the said acids with a base having a non-toxic, pharmacologically acceptable cation. In general, any base which will form a salt with a carboxylic acid and whose pharmacological properties will not cause an adverse physiological effects is within the scope of this invention.

Suitable bases thus include, for example, the alkali metal and alkaline earth metal hydroxides, carbonates, and the like, for example, calcium hydroxide, sodium hydroxide, sodium carbonate, potassium carbonate and the like, ammonia, primary, secondary and tertiary amines, such as monoalkylamines, dialkylamines, trialkylamines, for example, methylamine, diethylamine, triethylamine and the like, nitrogen containing heterocyclic amines, for examples, piperidine and the like. A salt thus produced is the functional equivalent of the corresponding compound of formula I wherein R is hydrogen and one skilled in the art will appreciate that the variety of salts embraced by the invention is limited only by the criterion that a base employed in forming the corresponding salts be both non-toxic and physiologically acceptable.

It is known that oxidative metabolism of arachidonic acid by the $\Delta^5$-lipoxygenase ($\Delta^5$-LO) pathway leads to the peptidoleukotrienes ($LTC_4$ and $LTD_4$) and leukotriene $B_4$ ($LTB_4$). $LTC_4$ and $LTD_4$ are potent bronchoconstrictors of human bronchi and contribute to edema in some species by increasing capillary permeability. $LTB_4$ is a potent chemotactic factor for inflammatory cells. $LTB_4$ has also been found in synovial fluid from wherein X, $R_1'$, $R_2'$, $R_1''$, $R_2''$, $R_7$, $R_8$, $R_9$, n and t are as previously described.

In Reaction Scheme VII, a compound of formula XXVI is reacted with a compound of formula XXIII to yield the corresponding compound of formula XXVII. The reaction is carried out utilizing an alkali metal carbonate as the base, for example, sodium carbonate, preferably potassium carbonate, with added sodium iodide or potassium iodide, in a solvent such as acetone, methyl ethyl ketone, dimethylformamide, toluene or the like, at a temperature in the range of from about 40° to about 70°. The solid-liquid phase-transfer catalyst tris[2-(2-methoxyethoxy)ethyl]amine can be used to facilitate the reaction when toluene is the solvent.

The hydrolysis of a compound of formula XXVII to the corresponding compound of formula XXVIII can be carried out utilizing standard conditions for example utilizing an alkali metal hydroxide such as sodium hydroxide or potassium hydroxide, in a solvent such as methanol, ethanol or the like, sometimes with added dioxane to aid solubility, at a temperature in the range of from about 25° to about 65°.

The conversion of a compound of formula XXVIII to the corresponding compound of formula Ib' can be accomplished by hydrogenation in a Parr apparatus at hydrogen pressure of 50 to about 60 psi using a palladium catalyst in a solvent such as ethanol, ethyl acetate, tetrahydrofuran or the like, at a temperature in the range of from about 25° to about 70°. A mineral and catalyst can be used in addition to the palladium catalyst.

patients with rheumatoid arthritis and gout and may be a mediator of inflammation and joint destruction in these diseases. Consequently, inhibitors of $\Delta^5$-LO may be of therapeutic value in the treatment of asthma and inflammatory diseases.

Furthermore, products of the $\Delta^5$-LO pathway (LTB$_4$, LTC$_4$, TLTD$_4$) are present in elevated levels in skin lesions of patients with psoriasis and atopic dermatitis and may be mediators of these skin diseases. The intracutaneous application of LTB$_4$ to human skin gives a wheal and flare reaction followed by infiltration of neutrophils into the site of application. The influx of neutrophils is also observed during the inflammatory reactions associated with psoriatic lesions. Topical application of LTB$_4$ to human skin causes abscesses similar to those of pustular psoriasis.

The compounds of formula I exhibit activity, for example, as $\Delta^5$-lipoxygenase inhibitors, and as hereinafter further described. The useful pharmacological activities of the compound of formula I can be demonstrated by the tests hereinafter set forth.

The compounds of formula I are useful as agents for the treatment of inflammatory diseases such as arthritis; inflammatory bowel disease such as colitis and as hereinafter further described; as anti-inflammatory agents in the topical therapeutic treatment of leukotriene-mediated dermal inflammations including psoriasis; and bronchopulmonary diseases such as asthma.

Inflammatory bowel disease (IBD) includes a variety of diseases of the gastrointestinal (GI) tract such as Crohn's disease of the colon and ileum, ulcerative colitis and pseudomembraneous colitis. Common symptoms of these diseases include inflammation of the affected area of the GI mucosa, mucosa ulceration, edema, infiltration of the mucosa with inflammatory cells and severe diarrhea. Arachidonic acid metabolites from the $\Delta^5$-LO pathway are believed to mediate IBD.

IN VITRO TEST FOR $\Delta^5$-LIPOXYGENASE INHIBITORS

In this procedure a compound is tested for its effect on $\Delta^5$ lipoxygenase from rat basophilic leukemia (RBL-1 cells). The activity of this enzyme was determined by measuring the catalytic conversion of [1-$^{14}$C]arachidonic acid to [1-$^{14}$C-5-hydroperoxy-6,8,11,14-eicosatetraenoic acid ([1-$^{14}$C]-5-HPETE) which leads to the formation of the 5-hydroxy derivative ([1-$^{14}$C]-5-HETE). The $\Delta^5$-lipoxygenase was derived from the supernatant fraction of lysed RBL-1 cells using a modification of the method previously described by Jakschik and Lee [Nature 287,51 (1980)]. Briefly, RBL-1 cells were lysed by homogenization in ice-cold buffer (50 mM Tris-HCl buffer. PH 7.2, containing 1 mM EDTA and 14 $\mu$M indomethacin). The homogenate was centrifuged at 4° at 49,000 g for 20 minutes and the resulting supernatant fraction was used as the source of $\Delta^5$-lipoxygenase. The enzyme was assayed at 37° using 6.7 $\mu$M (0.39 $\mu$Ci/ml) [1-$^{14}$C]arachidonic acid as the substrate in 50 mM Tris-HCl buffer. PH 7.2, containing 1 mM glutathione. 2 mM CaCl$_2$, 14 $\mu$M indomethacin, and 0.25 to 0.50 mM EDTA. The mixture was incubated for 10 minutes and the reaction was stopped by the addition of citric acid and diethyl ether. The ethereal extract containing [1-$^{14}$C]-5-HETE and unreacted substrate was analyzed by silica gel TLC using isooctanemethylethyl ketone-acetic acid (100:9:1) as the developing solvent. The major radioactive spots were located using a Berthold TLC scanner. The [1-$^{14}$C]-5-HETE was identified by co-chromatography with an authentic, chemically synthesized [1-$^{14}$C]-5-HETE standard. The R$_f$ values for [1-$^{14}$C]-5-HETE, unconverted [1-$^{14}$C]arachidonic acid, and unidentified radioactive polar products were 0.49, 0.95, and 0.04 respectively. The effect of an inhibitor on $\Delta^5$-lipoxygenase activity is determined by preincubating the enzyme for 10 minutes at 30° in the presence or absence of various concentrations of the drug prior to addition of substrate. This test has been described by: W. C. Hope, A. F. Welton, C. Fiedler-Nagy, C. Batuta-Bernardo and J. F. Coffey, Biochemical Pharmacology 32, 362 (1983).

In this test, (S)-6-[6-(2,3-dihydroxyphenyl)hexyloxy]-alpha-methyl-2-naphthaleneacetic acid exhibited an IC$_{50}$ value of 0.012$\mu$M.

RAT PERITONEAL MACROPHAGE ASSAY, IN VITRO

The rat peritoneal macrophage assay measures the ability of a test compound to influence the release of arachidonic acid (AA) from phospholipid stores in the plasma membrane and the subsequent metabolism of AA by the $\Delta^5$-lipoxygenase (5-LO) and cyclooxygenase (CO) pathways to the final products excreted by the cells: leukotriene B$_4$ (LTB$_4$, from the 5-LO pathway) and prostaglandin E$_2$ (PGE$_2$, from the CO pathway).

Macrophages were obtained form rats by peritoneal lavaqe with phosphate buffered saline minus Ca$^{+2}$ and Mg$^{+2}$ (PBS). Cells were washed 3 times with PBS and resuspended in Delbecco's Modified Eagle medium (Gibco Laboratories) containing L-glutamine and D-glucose and supplemented with 10% fetal calf serum. Cells were counted on a Coulter ZBA cell counter and then resuspended to a concentration of $4 \times 10^6$ cells/mL. Three mL of the cell suspension were added to plastic culture dishes (3 cm), and then the cells were allowed to adhere for 90 minutes at 37° C. Dishes were washed 3 times with PBS to remove nonadherent cells. $^{14}$C-AA (ca. 54$\mu$Ci/mmol) were added to the cells (1 $\mu$Ci/dish) and allowed to incorporate for 90 minutes. Unincorporated $^{14}$C-AA was removed and the cell layer was again washed 3 times with PBS. Test compounds were dissolved in DMSO and diluted in phosphate-buffered Hank's balanced salt solution to appropriate concentrations. Cells were incubated with test compounds or the solution used to dissolve the test compounds (control) for 30 minutes at 37° C. and were then stimulated with calcium ionophore A 23187 ($5 \times 10^{-7}$M) for 20 minutes. The extracellular fluid was removed and $^{14}$C radioactivity released into this fluid from AA metabolism was measured by liquid scintillation spectroscopy. The amounts of LTB$_4$ and PGE$_2$, were measured in the extracellular fluid by radioimmunoassay with specific antisera. The effect of a test compound or standard was calculated as a percent inhibition of the maximum effect produced in the presence of A 23187 and expressed as an inhibitory concentration 50% (IC$_{50}$).

This assay measures inhibition by the test compounds of the 5-LO and the CO pathways of AA metabolism and this inhibition is expressed as an IC$_{50}$ for LTB$_4$ and PGE$_2$ formation respectively. Data with some compounds of this invention is shown in Table I and shows that the predominant effect is on the 5-LO pathway.

ACETIC ACID-INDUCED COLITIS IN RATS, IN VIVO

The rat acetic acid induced colitis bioassay has been described by J. E. Krawisz, et al. in Amer. J. Proc. Gastro. Col. Rec. Surg. 31: 11–18 (1980), and by P. Sharon and W. F. Stenson in Gastroenterology 88: 55–63 (1985) and 86: 453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300g, were pretreated twice daily for two days with either the vehicle (water, or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. 24 hours after the acetic acid treatment, the animals were sacrificed, the colonic mucosa was surgically removed and homogenized in an aqueous buffer at pH 6 with a Tissumizer or similar device and myeloperoxidase was measured in the homogenate using o-phenylenediamine as a chromagen, as described by A. Voller, D. E. Bidwell and A. Bartlett in The Enzyme Linked Immunosorbent Assay (ELISA), Zoological Soc., London 1979, pages 29-30. Control animals were pretreated with the vehicle and saline in place of acetic acid.

Data for representative compounds of this invention is reported in Table I.

tered either singly or with other pharmaceutical agents, orally. Parenterally, rectally, or by inhalation, for example in the form of an aerosol micropulverized powder or nebulized solution. For oral administration the described compound can be administered in the form of tablets, capsules for example, in admixture with talc, starch, milk sugar or other inert ingredients, that is, pharmaceutically acceptable carriers, in the form of aqueous solutions, suspensions, elixirs or aqueous alcoholic solutions. for example, in admixture with sugar or other sweetening agents, flavoring agents, colorants, thickeners and other conventional pharmaceutical excipients or beadlets for oral administration. For parenteral administration, the desired compound can be administered in solutions or suspension, for example as an aqueous or peanut oil solution or suspension using excipients and carriers conventional for this mode of administration. For rectal administration, the desired compound can be administered in the form of suppositories utilizing an inert carrier material, cocoa butter and the like. For topical administration, the compounds of formula I can be incorporated into ointments creams, lotions qels and the like. In general, the solutions, ointments and creams which are useful in accordance with this invention include formulations having absorbable, water soluble or emulsion-type bases, such as petrolatum, lanolin, polyethylene glycols, or the like.

As used herein, a "compound of formula I" includes when applicable, enantiomers and racemates.

Suitable solutions will contain the compounds of formula I dissolved in a pharmaceutically acceptable solvent, such as polyethylene glycol, or the like.

Suitable lotions include, true solutions to aqueous or hydroalcoholic formulations containing finely divided particles. Lotions can contain suspending or dispersing agents such as cellulose derivatives, for example, methyl cellulose. ethyl cellulose or the like. Gels will typically be semi-solid preparations made by gelling a solution or suspension of a compound of formula I in a suitable hydrous or anhydrous vehicle, using a gelling agent such as a carboxy polymethylene, or the like, and

TABLE I

| Compound | Rat Peritoneal Macrophage Assay $IC_{50}$ ($\mu$M) | | | Rat Acetic Acid Colitis Model | |
|---|---|---|---|---|---|
| | $^{14}C$ | $LTB_4$ | $PGE_2$ | Dose mg/kg po | % Inhibition of Myeloperoxidase Accumulation |
| (S)-6-[6-(2,3-Dihydroxy-phenyl)hexyloxy]-α-methyl-2-naphthaleneacetic acid | 0.9 | 0.2 | 1 | 1 | 90 ± 11 |
| (S)-6-[6-(2,3-Dihydroxy-phenyl)hexyloxy]-α-methyl-2-naphthaleneacetic acid ethyl ester | 3 | 0.6 | 4 | 10 | 23 ± 5 |
| (rac)-6-[6-(2,3-Dihydroxy-phenyl)hexyloxy]-α-methyl-2-naphthaleneacetic acid | 1 | 0.6 | 3 | 10 | 88 ± 17 |
| 6-[6-(2,3-Dihydroxyphenyl)-hexyloxy]-2-naphthalene-acetic acid | 3 | 0.9 | 5 | 1 | 72 ± 8 |
| 6-[6-(2,3-Dihydroxyphenyl)-hexyloxy]-2-naphthalene-carboxylic acid | 3 | 3 | 9 | 1 | 72 ± 8 |
| (S)-6-[6-(3,4-Dihydroxyphenyl)-hexyloxy]-α-methyl-2-naphthaleneacetic acid | 1 | 0.6 | 3 | 10 | 13 ± 2 |

A compound of formula I or a salt thereof or a composition containing a therapeutically effective amount of a compound of formula I or a salt thereof can be administered by methods well known in the art. Thus, a compound of formula I or a salt thereof can be administhereafter neutralizing it to proper consistency with an alkali metal hydroxide, for example, sodium hydroxide, and an amine, for example, polyethylene cocoamine. Topical pharmaceutical compositions containing a compound of formula I can also be formulated to include conventional ingredients such as preservatives, stabilizers, wetting agents, emulsifying agents, buffers, and the like, in conventional amounts adjusted for particular requirements and which are readily determinable by those skilled in the art.

In the practice of the invention, the dose of a compound of formula I or a salt thereof to be administered and the frequency of administration will be dependent on the potency and duration of activity of particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

Furthermore, since some compounds of formula I of the invention, possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent. The formed diastereomers are separated by selective crystallization or chromatography and converted to the corresponding optical isomer Thus, the invention covers the racemates of the compounds of formula I as well as their optically active isomers (enantiomers).

The Examples which follow further illustrate the invention. All temperatures set forth in the specification and the Examples are in degrees Centiqrade. Melting points were taken on a Thomas Hoover capillary melting point apparatus and are uncorrected. All compounds were characterized by proton magnetic resonance spectra taken on a Varian XL-100 or SL-200 spectrometer and mass spectra taken on a CEC 21-110 mass spectrometer at 70eV. Preparative high-pressure liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

1-(6-Bromohexyl)-2,3-dimethoxvbenzene

A solution of 1.55M butyl lithium in hexane (195mL, 0.3 mol) was added dropwise over 30 minutes to a stirred solution of 1,2-dimethoxybenzene (41.4g, 0.3 mol) in 700 mL of anhydrous tetrahydrofuran at room temperature under argon. The reaction mixture was stirred and heated at 40° for 4 hours and then cooled to −70°. A solution of 46 mL (0.3 mol) of 1,6-dibromohexane in 250 mL of anhydrous tetrahydrofuran was added dropwise over 30 minutes. The cooling bath was removed and the reaction mixture was stirred for 1 hour and then heated at 40° for 4 hours. Most of the solvent was removed, 90mL of 3NHCl was added and the product was extracted with hexane. The extract was washed with sodium bicarbonate solution, dried and concentrated under reduced pressure to yield an oil. Distillation gave 1-(6-bromohexyl)-2,3-dimethoxybenzene as a yellow oil (29 g, 32% yield, b.p 125°-140°/0.15 mm).

This procedure is known and described for 1-(7-bromoheptyl)-2 3-dimethoxybenzene in the following reference: H. Halim, H. D. Locksley and J. J. Memon, J. Chem. Soc. Perkin I, 2331 (1980). It was used for the preparation of all of the bromo intermediates wherein n=3–10.

EXAMPLE 2

1-(6-Bromohexyl)-2,3-bis(phenylmethoxy)benzene

Boron tribromide (266 mL. 0.266 mol 1M in methylene chloride) was added dropwise over 1 hour to a cooled (−65°) solution of 40.0 g (0.133 mol) of 1-(6-bromohexyl)-2,3-dimethoxybenzene in 800 mL of anhydrous methylene chloride which was stirred in an argon atmosphere. The cooling bath was then removed and the reaction mixture was stirred for 1.5 hours. After cooling in an ice bath, 100 mL of water and 50 mL of 3N HCl were added and the mixture was stirred for 2 hours. The organic layer was separated, dried and concentrated under reduced pressure to an oil which was purified by HPLC using 5% methanol-chloroform to yield 34.7 g of 1-(6-bromohexyl)-2,3-dihydroxybenzene as an oil.

A mixture of 31.3 g (0.115 mol) of 1-(6-bromohexyl)-2,3-dihydroxybenzene, 41 mL (0.34 mol) of benzyl bromide, 47.5 g (0.34 mol) of potassium carbonate and 4.4 mL (13.6 mmol) of tris[2-(2-methoxyethoxy)ethyl]amine (TDA-1) in 750 mL of toluene was stirred at reflux for 40 hours. The reaction mixture was washed with half-saturated brine, dried and concentrated under reduced pressure to which was purified by HPLC using 25% toluene-hexane to give 34.6 g (67% yield) of 1-(6-bromohexyl)-2,3-bis(phenylmethoxy)benzene as an oil.

Anal. Calcd for $C_{26}H_{29}BrO_2$: C, 68.87; H, 6.45; Br, 17.62. Found: C, 69.11; H, 6.60; Br, 17.45.

EXAMPLE 3

1-[(2-Methanesulfonyloxy)ethyl]-2,3-dimethoxybenzene

To 20 g (0.145 mol) of 1,2-dimethoxybenzene in 300 mL of anhydrous tetrahydrofuran stirred at room temperature under argon was added 90 mL (0.145 mol) of 1.6 M butyl lithium in hexane over 30 minutes. The reaction mixture was stirred and heated at 40° for 4 hours and then cooled in an ice bath. Ethylene oxide (14 mL. 0.29 mol) was allowed to distill into the ice cooled reaction mixture over 45 minutes. The reaction mixture was stirred with ice bath cooling for 1.5 hours and then at room temperature for 17 hours. Most of the solvent was removed under reduced pressure and water was added to the residue. The product was extracted with ether and the dried extract was concentrated under reduced pressure to an oil. The remaining 1,2-dimethoxybenzene (7.5 g) was removed by distillation (bP 45°-60°/0.2 mm) and the residue was purified by HPLC using 20% ethylacetate-toluene to give 5 g (19% yield) of 1-(2-hydroxyethyl)-2,3-dimethoxybenzene. This intermediate (5 g, 0.028 mol) was dissolved in 100 mL of anhydrous methylene chloride and the solution was cooled in an ice bath. Triethylamine (7.7 mL, 0.056 mol) was added and followed by 2.6 mL (0.033 mol) of methane sulfonyl chloride added dropwise. The reaction mixture was stirred with ice bath cooling for two hours and then was washed with water, with sodium bicarbonate solution, dried and concentrated under reduced pressure to give (7.2 g) of 1-[(2-methanesulfonyloxy)ethyl]-2,3-dimethoxybenzene as an oil which was used without purification.

EXAMPLE 4

1-(6-Bromohexyl)-2,3-bis(acetyloxy)benzene

To 1.0 g (3.8 mmol) of 1-(6-bromohexyl)-2,3-dihydroxybenzene in 150 mL of ethyl acetate and 15 mL of acetic anhydride was added 0.03 mL of 70% perchloric acid. The solution was left at room temperature for 1.5 hours and then was washed with sodium bicarbonate solution. After drying, the organic layer was concentrated to give 1.3 g of 1-(6-bromohexyl)-2,3-bis-(acetyloxy)benzene as an oil.

EXAMPLE 5

1-[(2-Methanesulfonyloxy)ethyl]-3,4,-dimethoxybenzene

To 3.3 g (0.018 mol) of 3,4-dimethoxyphenethyl alcohol in 50 mL of methylene chloride and 4.2 mL (0.03 mol) of triethylamine cooled in an ice bath was added 1.6 mL (0.02 mol) of methanesulfonyl chloride with stirring. The reaction mixture was stirred for 75 minutes and then washed successively with water, 1N hydrochloric acid and sodium bicarbonate solution. After drying, the extract was concentrated under reduced pressure to give 1-[(2-methanesulfonyloxy)ethyl]-3,4-dimethoxy-benzene as an oil.

EXAMPLE 6

1-(6-Bromo-1-oxohexyl)-3,4-dimethoxybenzene

A mixture of 1.0 mL (7.8 mmol) of 1,2-dimethoxybenzene and 2.0 g (10 mmol) of 6-bromohexanoic acid was warmed briefly until homogeneous and stirred while 1.7 mL (11.7 mmol) of trifluoroacetic anhydride was added. The reaction mixture was stirred at room temperature for 17 hours and then was poured into sodium bicarbonate solution. The product was extracted with ethyl acetate and the dried extract was concentrated to an oil which was purified by chromatography on 150 g of silica gel. Elution with 25% ethyl acetate-hexane gave 1.6 g (65% yield) of 1-(6-bromo-1-oxohexyl)-3,4-dimethoxybenzene. The nmr spectrum was consistent with the structure.

EXAMPLE 7

4-(3,4-Dimethoxyphenyl)-3-butyn-1-ol

A mixture of 10 g (46 mmol) of 1-bromo-3,4-dimethoxybenzene, 3.4 g (48 mmol) of 3-butyn-1-ol and 8 mL (58 mmol) of triethylamine in 20 mL of methylene chloride was stirred and flushed with argon. To the mixture there was added 0.12 g (0.06 mmol) of cuprous iodide and 0.30 g (0.43 mmol) of bis(triphenylphosphine)palladium dichloride. The reaction mixture was stirred at room temperature for 4 hours and at reflux for 16 hours. After filtration, the filtrate was washed with water, dried and concentrated. The crude product was purified by HPLC using 30% ethyl acetate-toluene to give 3.0 g (32% yield) of 4-(3,4-dimethoxyphenyl)-3-butyn-1-ol.

EXAMPLE 8

4-(3,4-Dimethoxyphenyl)butan-1-ol

A mixture of 2.0 g of 4-(3,4-dimethoxyphenyl)-3-butyn-1-ol and 0.2 g of 10% palladium on carbon in 40 mL of ethanol was stirred in a hydrogen atmosphere for 4 hours. After filtration, the filtrate was concentrated under reduced pressure to give 1.9 g of 4-(3,4-dimethoxyphenyl)butan-1-ol as an oil.

EXAMPLE 9

4-(2,3-Dimethoxyphenyl)butan-1-ol

To 0.8 g (0.12 g-atoms) of lithium ribbon cut in small pieces in 50 mL of anhydrous ether stirred at room temperature under an argon atmosphere was added 12 g (0.06 mol) of 3-bromo-propan-1-ol 1-ethoxy ethyl ether [P. E. Eaton. G. F. Cooper, R. C. Johnston, and R. H. Mueller, J. Org. Chem. 37, 1947 (1972)]. After about 1 mL was added, the reaction mixture was cooled in an ice-salt bath and the rest of the bromo compound was added dropwise over 35 minutes. Stirring was continued with cooling for 1.5 hours and then 7.5 g (0.045 mol) of 2,3-dimethoxybenzaldehyde in 45 mL of anhydrous ether was added dropwise over 30 minutes. After 1 hour, the cooling bath was removed and stirring was continued at room temperature for 1 hour. The reaction mixture was poured into half-saturated ammonium sulfate solution. The ether layer was separated, dried ($Na_2SO_4$) and concentrated to an oil (13.9 g). Ethanol (25 mL), water (25 mL) and 2 mL of concentrated hydrochloric acid were added and the solution was left at room temperature for 35 minutes. Potassium carbonate was added with stirring until the mixture was basic. The ethanol was removed under reduced pressure and the product was extracte with ethyl acetate. The dried extract was concentrated to an oil (12.0 g). This was dissolved in 150 mL of ethanol. 1g of 10% palladium on carbon was added and the mixture was shaken on a Parr hydrogenator under an initial hydrogen pressure of 55 psi for 5 hours. The reaction mixture was filtered through Celite and the filtrate was concentrated to an oil. Purification by HPLC using 30% ethlacetate-hexane gave 7.45 g (79% yield) of 4-(2,3-dimethoxyphenyl)butan-1-ol.

This procedure has been reported in the literature to prepare 7-(2,3-dimethoxyphenyl)heptan-1-ol. J. H. P. Tyman and C. H. Khor, Chem. Ind. (1974), 526.

EXAMPLE 10

4-(6-Bromohexyl)-2,3-dimethoxy-1,1'-biphenyl

A solution of 2.5M butyl lithium in hexane (16 mL, 0.04 mol) was added dropwise over 15 min. to a stirred solution of 8.3 g (0.039 mol) of 2,3-dimethoxybiphenyl [J. M. Bruce and F. K. Sutcliffe, J. Chem. Soc. 4435 (1955)] in 160 mL of anhydrous tetrahydrofuran cooled at 0° under argon. The reaction mixture was stirred at 0° for 2.5 hours and then refluxed for 30 min. After cooling to 5°, 6.3 mL (0.039 mole) of 1,6-dibromohexane was added. Stirring was continued at 5° for 30 min. at 25° for 30 min. and at reflux for 20 hours. Workup as in Example 1 gave an oil. Purification by HPLC using 3% ethyl acetatehexane gave 5.7 g of unreacted 2,3-dimethoxybiphenyl and 3.3 g of 4-(6-bromohexyl)-2,3-dimethoxy-1,1'-biphenyl as an oil. The structure was confirmed by the nmr and mass spectra (molecular ion at m/e 376).

EXAMPLE 11

1-(5-Bromopentyl)-6-chloro-2,3-dimethoxybenzene

To 4.0 g of 1-(5-bromopentyl)-2,3-dimethoxybenzene in 50 mL of methylene chloride cooled in an ice bath was added 18 mL of 0.8M chlorine in methylene chloride. The reaction mixture was kept at 0° for 3 hours and then was concentrated under reduced pressure to yield an oil. Purification by HPLC using 30% toluene-hexane gave 2.60 g (58% yield) of 1-(5-bromopentyl)-6-chloro-2,3-dimethoxybenzene. The nmr spectrum was consistent with the structure and the mass spectrum gave a molecular ion at m/z 320 ($C_{13}H_{18}BrClO_2$).

EXAMPLE 12

1-(5-Bromopentyl)-5,6-dichloro-2,3-dimethoxybenzene

To 4.0 g of 1-(5-bromopentyl)-2,3-dimethoxy benzene in 50 mL of methylene chloride cooled in an ice bath was added 18 mL of 0.8M chlorine in methylene chloride. After 15 minutes, 17 mL of 0.88M chlorine in methylene chloride was added. The reaction mixture was kept at 0° for 3 hours and then was concentrated under reduced pressure to yield an oil. Purification by HPLC using 30% toluene-hexane gave 2.03 g (41% yield) of 1-(5-bromopentyl)-5,6-dichloro-2,3-dimethoxybenzene. The nmr spectrum was consistent with the structure and the mass spectrum gave a molecular ion at m/z 354 ($C_{13}H_{17}BrCl_2O_2$).

EXAMPLE 13

1-(5-Bromopentyl)-2,3-dimethoxy-4,5,6-trichlorobenzene

To 1.9 g of 1-(5-bromopentyl)-2,3-dimethoxy benzene in 25 mL of methylene chloride cooled in an ice bath was added 23 mL of 0.88M chlorine in methylene chloride. After 1.5 hours at 0°, 5 mL of 1.35M chlorine in methylene chloride was added. The reaction mixture was kept at 0° for 17 hours and then was concentrated under reduced Pressure to yield an oil. Purification by HPLC using 25% toluene-hexane gave 1.48 g (56% yield) of 1-(5-bromopentyl)-2,3-dimethoxy-4,5,6-trichlorobenzene. The nmr spectrum was consistent with the structure and the mass spectrum gave a molecular ion at m/z 388 $C_{13}H_{16}BrCl_3O_2$).

EXAMPLE 14

6-(6-Chloro-3,4-dimethoxyphenyl)hexan-1-ol

To 1.40 g of 6-(3,4-dimethoxyphenyl)hexan-1-ol in 25 mL of methylene chloride cooled in a ethanol-dry ice bath was added 4.6 mL of 1.35M chlorine in methylene chloride. The reaction mixture was kept at −75° for 1.5 hours, at −18° for 16 hours and then at 0° for 24 hours. After concentration under reduced pressure, the crude product was purified by HPLC to give 6-(6-chloro-3,4-dimethoxyphenyl)hexane-1-ol as an oil. The nmr spectrum was consistent with the structure and the mass spectrum gave a molecular ion at m/z 272 ($C_{14}H_{21}ClO_3$).

EXAMPLE 15

6-Bromo-1-[3,4-dimethoxy-5-(1-methylethyl)phenyl]-1-hexanone

A solution of 5.0 g (0.028 mol) of 3-(1-methylethyl)-1,2-dimethoxybenzene in 5 mL of methylene chloride was added to an ice cooled mixture of 4.4 g (0.033 mol) of aluminum chloride and 7.0 g (0.033 mol) of 6-bromohexanoyl chloride in 50 mL of methylene chloride. The reaction mixture was kept at 0° for 18 hours. Water was added and the organic layer was separated and washed with sodium bicarbonate solution. The dried extract was concentrated under reduced pressure to an oil which was purified by HPLC using 5% ethyl acetate-hexane to give 8.1 g (82% yield) of 6-bromo-1-[3,4-dimethoxy-5-(1-methylethyl)-phenyl]-1-hexanone as an oil. The nmr spectrum was consistent with the structure and the mass spectrum gave the molecular ion at m/z 356 ($C_{17}H_{25}BrO_3$).

EXAMPLE 16

6-Bromo-1-(3,4-dimethoxy-2,5-dimethylphenyl)-1-hexanone

A solution of 0.227 g (1.5 mmol) of 3,6-dimethylveratrole in 1 mL of methylene chloride was added to an ice cooled mixture of 0.245 g (1.8 mmol) of aluminum chloride and 0.416 g (1.9 mmol) of 6-bromohexanoyl chloride in 3 mL of methylene chloride. The reaction mixture was kept at 0° for 19 hours. Water was added and the organic layer was separated and washed with sodium bicarbonate solution. The dried extract was concentrated to an oil which was chromatographed on 60 g of silica gel using 10% ethyl acetate-hexane to give 0.235 g of 6-bromo-1-(3,4-dimethoxy-2,5-dimethylphenyl)-1-hexanone as an oil. The nmr spectrum was consistent with the structure and the mass spectrum gave the molecular ion at m/z 342 ($C_{16}H_{23}BrO_3$).

EXAMPLE 17

6-Bromo-1-(3,4-dimethoxy-2,5,6-trimethylphenyl)-1-hexanone

A solution of 2.956 g (16 mmol) of 1,2-dimethoxy-3,4,6trimethylbenzene in 10 mL of methylene chloride was added to 2.40 g (18 mmol) of aluminum chloride and 3.80 g (18 mmol) of 6-bromohexanoyl chloride in 30 mL of methylene chloride cooled in an ice bath. The solution was kept at 3° for 45 minutes and then at 23° for 42 hours. An additional 2.0 g of aluminum chloride and 3.0 g of 6-bromohexanoyl chloride were added and the reaction mixture was stirred at reflux for 22 hours. Workup as in Example 16 and purification by HPLC using 4% ethyl acetate-hexane gave 0.95 g of 6-bromo-1-(3,4-dimethoxy-2,5,6-trimethylphenyl)-1-hexanone as an oil. The nmr spectrum was consistent with the structure and the mass spectrum gave a molecular ion at m/z 356 ($C_{17}H_{25}BrO_3$).

EXAMPLE 18

6-Bromo-1-(2-fluoro-4,5-dimethoxyphenyl)-1-hexanone

A solution of 5.3 g (0.034 mol) of 1,2-dimethoxy-4-fluorobenzene in 25 mL of methylene chloride was added to a solution of 5.4 g (0.041 mol) of aluminum chloride and 8.7 g (0.041 mol) of 6-bromohexanoyl chloride in 60 mL of methylene chloride cooled in an ice bath. The resulting solution was kept at 0° for 5 hours and then worked up as in Example 16. The crude product was recrystallized from methylene chloride-ether to give 6.98 g (62% yield), mp 81°–83°, of 6-bromo-1-(2-fluoro-4,5-dimethoxyphenyl)-1-hexanone. The nmr spectrum was consistent with the structure and the mass spectrum gave a molecular ion at m/z 332 ($C_{14}H_{18}BrFO_3$).

EXAMPLE 19

2-Chloro-3,4-dimethoxybenzene hexanol

To 0.6 g (0.08 g-atoms) of lithium ribbon cut in small pieces in 40 mL of anhydrous ether stirred at room temperature under an argon atmosphere was added 9.50 g (0.04 mol) of 5-bromo pentanol 2-ethoxyethyl ether. After about 1 mL was added, the reaction mixture was cooled to −5° and the rest of the bromo compound was added dropwise. Stirring at −5° was continued for 1 hour and then 6.0 g (0.03 mol) of 2-chloro-3,4-dimethoxybenzaldehyde [J. Weinstock et at., J. Med. Chem. 29,2315 (1986)] in 50 mL of ether-20 mL of tetrahydrofuran was added dropwise over 1 hour. The cooling bath was removed and stirring was continued for 1 hour. The reaction mixture was worked up as in Example 9 to yield an oil which was dissolved in 25 mL of ethanol, 20 mL of water and 2 mL of concentrated hydrochloric acid was added. The solution was left at 25° for 45 minutes. Potassium carbonate was added with stirring until the mixture was basic. The ethanol was removed under reduced pressure and the product was extracted with ethyl acetate. The dried extract was concentrated to an oil (10 g). This was purified by HPLC using 60% ethyl acetate-hexane to give 2.9 g (34% yield) mp 75°-80° of 6-(2-chloro-3,4-dimethoxybenzene)-6-hydroxyhexanol. This was dissolved in 50 mL of ethanol 0.3 g of 10% palladium on carbon was added and the mixture was shaken under an initial hydrogen Pressure of 54 psi for 21 hours. The reaction mixture was filtered through Celite and the filtrate was concentrated under reduced pressure to an oil. Purification by HPLC using 15% ethyl acetate-toluene gave 1.74 g (64% yield) of 2-chloro-3,4-dimethoxybenzene hexanol as an oil. The structure was confirmed by nmr and mass spectra (molecular ion at m/e 272).

EXAMPLE 20

(S)-6-Hydroxy-alpha-methyl-2-naphthaleneacetic acid methyl ester

To a solution of 11.3 g (0.049 mol) of (S)-6-methoxy-alpha-methyl-2-naphthalene acetic acid in 300 mL of methylene chloride cooled at −70° was added 110 mL (0.11 mol) of 1M boron tribromide over 10 minutes. The reaction mixture was allowed to warm to 5° and stirred for one hour. Stirring was continued at 24° for 2 hours and 100 mL of water and 25 mL of 3N hydrochloric acid were added. The mixture was stirred at 24° for 1.5 hours, 200 mL of ether was added and the organic layer was separated, dried and concentrated to a solid. Recrystallization from ether-methylene chloride gave 8.7 g (82% yield), mp 170°-180°, of (S)-6-hydroxy-alpha-methyl-2-naphthaleneacetic acid.

A solution of 3.9 g (18 mmol) of (S)-6-hydroxy-alpha-methyl-2-naphthalene acetic acid in 50 mL of methanol and 0.5 ml of concentrated sulfuric acid was stirred at reflux for 24 hours. The methanol was removed under reduced pressure and the residue was dissolved in ethyl acetate and the solution was washed with sodium bicarbonate solution, dried and concentrated under reduced pressure to yield an oil. Purification by chromatography on silica gel using 25% ethylacetate-hexane gave 3.7 g (90% yield), mp 82-85; of (S)-6-hydroxy-alpha-methyl-2-naphthalene acetic acid methyl ester. $+[\alpha]_D 68.6°$ (in chloroform).

EXAMPLE 21

(S)-6-Hydroxy-alpha-methyl-2-naphthalene acetic acid ethyl ester

A solution of 10.5 g of (S)-6-hydroxy-alpha-methyl-2-naphthalene acetic acid in 100 mL of ethanol and 1.5 mL of concentrated sulfuric acid was refluxed for 48 hours. Sulfuric acid (2.5 mL) was added and reflux was continued for 24 hours. The ethanol was removed under reduced pressure, ethyl acetate was added and the solution was washed with sodium bicarbonate solution, dried and concentrated at reduced pressure to a solid. Purification by chromatography on 300 g of silica gel using 20% ethyl acetate-hexane gave 8.0 g (67% yield), mp 93°-98°, of (S)-6-hydroxy-alpha-methyl-2-naphthalene acetic acid ethyl ester. $[\alpha]_D+39.5°$ (in chloroform)

EXAMPLE 22

(S)-alpha-methyl-6-[6-[2,3-bis(phenylmethoxy)phenyl]-hexyloxy]-2-naphthaleneacetic acid methyl ester A mixture of 3.25 g (7.17 mmol) of 1-(6-bromohexyl)-2,3-bis-(phenylmethoxy)benzene, 1.50 g (6.5 mmol) of (S)-alpha-methyl-6-hydroxy-2-naphthaleneacetic acid methyl ester, 1.08 g (7.17 mmol) of sodium iodide and 2.70 g (19.6 mmol) of potassium carbonate in 60 mL of acetone - 6 mL of dimethylformamide was stirred at reflux for 48 hours. The reaction mixture was filtered and the filtrate was concentrated at reduced pressure. The residue was purified by HPLC using 20% ethyl acetate-hexane to give 3.24 g (75% yield) of (S)-alpha-methyl-6-[6-[2,3-bis(phenylmethoxy)phenyl]hexyloxy]-2-naphthaleneacetic acid methyl ester as an oil. The nmr and mass spectra were consistent with the structure.

EXAMPLE 23

(S)-alpha-methyl-6-[6-[2,3-bis(phenylmethoxy)phenyl]-hexyloxy]-2-naphthaleneacetic acid A solution of 5.5 g (9.1 mmol) of (S)-alpha-methyl-6-[6-[2,3-bis(phenylmethoxy)phenyl]hexyloxy]-2-naphthaleneacetic acid methyl ester in 135 mL of methanol and 45 mL (45 mmol) of 1N sodium hydroxide was refluxed for 3 hours. The solvent was removed at reduced pressure and the residue was acidified and extracted with ether. The dried extract was concentrated at reduced pressure to an oil which was crystallized from ether-hexane to give 4.9 g (91% yield), mp 66°-70°, of (S)-alpha-methyl-6-[6-[2,3-bis(phenylmethoxy)phenyl]hexyloxy]-2-naphthaleneacetic acid.

Anal. Calcd for $C_{39}H_{40}O_5$: C, 79.56; H, 6.85. Found: C. 79.29; H. 6.92.

EXAMPLE 24

(S)-6-[6-(2,3-Dihydroxvphenyl)hexyloxy]-alpha-methyl-2-naphthaleneacetic acid

A mixture of 4.9 g (8.3 mmol) of (S)-alpha-methyl-6-[6-[2,3-bis(phenylmethoxy)phenyl]hexyloxy]-2-naphthaleneacetic acid and 0.5 g of 10% palladium on carbon in 100 mL of ethyl acetate was shaken in a hydrogen atmosphere for 22 hours. The reaction mixture was filtered through Celite and the filtrate was concentrated at reduced pressure to an oil which was crystallized from ether-hexane to give 2.9 g (85% yield), mp 136°-139°, of (S)-[6-(2,3-dihydroxyphenyl)hexyloxy]-alpha-methyl-2-naphthaleneacetic acid.

Anal. Calcd for: $C_{25}H_{28}O_5$: C, 73.51; H, 6.91. Found: C, 73.56; H. 6.92.

EXAMPLE 25

(S)-alpha-methyl-6-[6-[2,3-bis(phenylmethoxy)phenyl]-hexyloxy]-2-napthaleneacetic acid ethyl ester A mixture of 7.5 g (16.5 mmol) of 1-(6-bromohexyl)-2,3-bis(phenylmethoxy)benzene. 3.7 g (15 mmol) of (S)-alpha-methyl-6-hydroxy-2-naphthaleneacetic acid ethyl ester, 2.5 g (16.5 mmol) of sodium iodide and 6.5 g (45 mmol) of potassium carbonate in 200 mL of acetone - 200 mL of dimethylformamide was stirred at reflux for 43 hours. The reaction mixture was filtered and the filtrate was concentrated at reduced pressure.

Purification by HPLC using 10% ethyl acetate-hexane gave 7.2 g (78% yield) of (S)-alpha-methyl-6-[6-[2,3-bis-(phenylmethoxy)phenyl]hexyloxy[-2-naphthaleneacetic acid ethyl ester as an oil. The mass spectrum showed a molecular ion at m/e 616 ($C_{41}H_{44}O_5$) and the nmr spectrum was consistent with the structure.

EXAMPLE 26

(S)-6-[6-(2,3-Dihydroxyphenyl)hexyloxy]-alpha-methyl-2-naphthaleneacetic acid ethyl ester A mixture of 1.2 g of (S)-alpha-methyl-6-[6-[2,3-bis(-phenylmethoxy)phenyl]hexyloxy]-2-nnaphthaleneacetic acid ethyl ester and 0.3 g of 10% palladium on carbon in 50 mL of ethyl acetate was shaken in a hydrogen atmosphere for 21 hours. The reaction mixture was filtered through a Celite pad and the filtrate was concentrated at reduced pressure to an oil. Crystallization from ether-hexane gave 0.59 g of (S)-6-[6-(2,3-dihydroxyphenyl)-hexyloxy]-alpha-methyl-2-naphthaleneacetic acid ethyl ester as a semisolid.

Anal. Calcd for $C_{27}H_{32}O_5$: C, 74.29; H. 7.39. Found: C, 74.15; H, 7.67.

EXAMPLE 27

(rac).-6-Hydroxy-alpha-methyl-2-naphthaleneacetic acid methyl ester

A suspension of 5.1 g of (rac)-6-methoxy-alpha-methyl-2-naphthaleneacetic acid [I. T. Harrison et. al. J. Med. Chem. 13, 203 (1970)] in 50 mL of acetic acid and 25 mL of 48% hydrobromic acid was saturated with hydrobromic acid gas and then stirred at reflux for 3 hours. The reaction mixture was poured into ice-water and the Product was removed by filtration to give 4.69 g (98% yield), mp 165°–170°, of rac.-6-hydroxy-alpha-methyl-2-naphthaleneacetic acid.

A mixture of 4.67 g (0.0216 mol) of rac-6-hydroxy-alpha-methyl-2-naphthaleneacetic acid. 13.4 mL (0.216 mole) of methyliodide, 7.3 g (0.086 mol) of sodium bicarbonate in 50 mL of dimethylformamide was stirred and heated at 45° for 24 hours. The solvent was removed on the oil pump and the residue was treated with water and extracted with ether. The dried extract was concentrated to an oil which was purified by HPLC using 15% ethyl acetate-hexane to give 5.0 g, mp 61°–66°, of (rac)-6-hydroxy-alpha-methyl-2-naphthaleneacetic acid methyl ester

EXAMPLE 28

(rac)-alpha-methyl-6-[6-[2,3-bis(phenylmethoxy)-phenyl]hexyloxy]-2-naphthaleneacetic acid methyl ester A mixture of 3.10 g (6.8 mmol) of 1-(6-bromohexyl)-2,3bis(phenylmethoxy)benzene, 1.50 g (6.5 mmol) of rac.-6-hydroxy-alpha-methyl-2-naphthaleneacetic acid methyl ester 1.8 g (13 mmol) of potassium carbonate and 0.98 g (6.5 mmol) of sodium iodide in 35 mL of acetone - 10 mL of dimethylformamide was stirred at reflux for 43 hours. The reaction mixture was filtered and the filtrate was concentrated at reduced pressure. Purification by HPLC using 10% ethyl acetate-hexane gave 3.40 g (87% yield), mp 56°–58°, of (rac)-alpha-methyl-6-[6[2,3-bis(phenylmethoxy)phenyl]hexyloxy]-2-naphthaleneacetic acid methyl ester.

Anal. Calcd for $C_{40}H_{42}O_5$: C, 79.71; H, 7.02. Found: C, 79.41; H. 6.92.

EXAMPLE 29

(rac)-alpha-methyl-6-[6-[2,3-bis(phenylmethoxy)-phenyl]hexyloxy]-2-naphthaleneacetic acid A solution of 3.35 g (5.56 mmol) of rac.-alpha-methyl-6-[6[2,3-bis(phenylmethoxy)phenyl]hexyloxy]-2-naphthaleneacetic acid methyl ester in 100 mL of methanol and 3.7 mL (22 mmol) of 6N sodium hydroxide was stirred at reflux for 4 hours. The solvent was removed at reduced pressure, the residue was acidified and the product was filtered to give (rac)-alpha-methyl-6-[6-[2,3-bis(phenylmethoxy)phenyl]hexyloxy]-2-naphthaleneacetic acid. An analytical sample was obtained from ether-hexane.

Anal. Calcd. for $C_{39}H_{40}O_5$: C, 79.56; H, 6.85. Found: C, 79.24; H, 6.73.

EXAMPLE 30

(rac)-6-[6-(2,3-Dihydroxyphenyl)hexyloxy]-alpha-methyl-2-naphthalene-acetic acid A mixture of 3.3 of rac.-alpha-methyl-6-[6-[2,3-bis(-phenylmethyl)phenyl]hexyloxy]-2-naphthaleneacetic acid and 0.8 g of 10% palladium on carbon in 150 mL of ethyl acetate was stirred in a hydrogen atmosphere for 19 hours. The reaction mixture was filtered throuh Celite and the filtrate was concentrated at reduced pressure to a solid which was recrystallized from ether-hexane to give 1.3 g (57% yield), mp 134°–143°, of (rac)-6-[6(2,3-dihydroxyphenyl)hexyloxy]-alpha-methyl-2-naphthaleneacetic acid.

Anal. Calcd. for $C_{25}H_{28}O_5$: C, 73.51; H, 6.91. Found: C, 73.00; H, 6.73.

EXAMPLE 31

6-Hydroxy-2-napthaleneacetic acid ethyl ester

A mixture of 4.55 g (22.5 mmole) of 6-hydroxy-2-naphthaleneacetic acid. [P. Muller et. al., Helv. Chim. Acta, 57, 790 (1974)] 7.6 g (90 mmol) of sodium bicarbonate and 18 mL (0.225 mol) of ethyl iodide in 50 mL of dimethylformamide was stirred and heated at 55° for 18 hours. The solvent was removed at reduced pressure, water was added to the residue and the crude product was filtered and recrystallized from ether-hexane to give 4.49 g (87% yield), mp 81°–83°, of 6-hydroxy-2-naphthaleneacetic acid ethyl ester.

EXAMPLE 32

6-[6-[2,3-bis-Phenylmethoxy)phenyl]hexyloxy]-2-naphthalene acetic acid

A mixture of 5.82 g (12.8 mmol) of 1-(6-bromohexyl)-2,3-bis(phenylmethoxy)benzene. 2.70 g (11.7 mmol) of 6-hydroxy-2-napthaleneacetic acid ethyl ester, 3.3 (23.5 mmol) of potassium carbonate and 1.8 g (11.7 mmol) of sodium iodide in 70 mL of acetone - 20 mL of dimethylformamide was stirred at reflux for 48 hours. The reaction mixture was filtered. the filtrate was concentrated at reduced Pressure and the residue was purified by HPLC using 10% ethyl acetate-hexane to give 5.85 g (83% yield), mp 53°–55°, of 6-[6-[2,3-bis(phenylmethoxy)-phenyl]hexyloxy]-2-naphthaleneacetic acid ethyl ester.

Anal. Calcd. for $C_{40}H_{42}O_5$: C, 79.42; H, 6.66. Found: C, 79.62; H, 6.58.

EXAMPLE 33

6-[6-(2 3-Dihydroxyphenyl)hexyloxy]-2-naphthalene acetic acid

A mixture of 2.57 g of 6-[6-[2,3-bis(phenylmethoxy)-phenyl]-hexyloxy]-2-naphthaleneacetic acid and 0.7 g of 10% palladium on carbon in 125 mL of ethyl acetate was shaken in a hydrogen atmosphere for 22 hours. The reaction mixture was filtered through a Celite pad and the filtrate was concentrated at reduced pressure to a solid which was recrystallized from ether-hexane to give 1.44 g (82% yield), mp 119°–121°, of 6-[6-(2,3-dihydroxyphenyl)hexyloxy]-2-naphthalene acetic acid.

Anal. Calcd. for $C_{24}H_{26}O_5$: C, 73.08; H, 6.64. Found: C, 72.80; H, 6.61.

EXAMPLE 34

6-[6-[2,3-bis(Phenylmethoxy)phenyl]hexyloxy]-2-naphthalene carboxylic acid

A mixture of 5.74 g (12.7 mmol) of 1-(6-bromohexyl)-2,3-bis-(phenylmethoxy)benzene, 2.50 g (11.6 mmol) of 6-hydroxy-2-naphthalenecarboxylic acid ethyl ester [G. W. Gray and B. Jones, J Chem. Soc., 678 (1954)], 3.2 g (23.2 mmol) of potassium carbonate and 1.75 g (11.6 mmol) sodium iodide in 70 mL of acetone - 20 mL of dimethylformamide was stirred at reflux for 48 hours. The reaction mixture was concentrated at reduced pressure. The crude product was purified by HPLC using 10% ethylacetate-hexane to give 6.26 g (92% yield), mp 66°–68°, of 6-[6-[2,3-bis(phenylmethoxy)phenyl]hexyloxy]-2-naphthalenecarboxylic acid.

Anal. Calcd. for $C_{37}H_{36}O_5$: C, 79.26; H, 6.47. Found: C, 78.99; H, 6.18.

EXAMPLE 35

6-[6-(2,3-Dihydroxyphenyl)hexyloxy]-2-naphthalenecarboxylic acid

A mixture of 2.6 g of 6-[6-[2,3-bis(phenylmethoxy)-phenyl]-hexyloxy]-2-naphthalenecarboxylic acid, 0.7 g of 10% palladium on carbon in 125 mL of tetrahydrofuran was shaken in a hydrogen atmosphere for 17 hours. The reaction mixture was filtered through a Celite pad and the filtrate was concentrated at reduced pressure to a solid. Recrystallization from ether-hexane gave 1.34 g (76% yield), mp 167°–171°, of 6-[6-(2,3-dihydroxyphenyl)hexyloxy]-2-naphthalenecarboxylic acid.

Anal. Calcd. $C_{23}H_{24}O_5$: C, 72.61; H, 6.36. Found: C, 72.34; H, 6.38.

EXAMPLE 36

1-(6-Bromohexyl)-3,4-dimethoxybenzene

A mixture of 32.9 g of 1-(6-bromo-1-oxohexyl)-3,4-dimethoxybenzene, 3.0 g of 10% palladium on carbon and 5 drops of concentrated sulfuric acid in 200 mL of acetic acid was shaken under hydrogen pressure for 9 hours in a Parr hydrogenator at an initial pressure of 55 psi. The reaction mixture was filtered through Celite and the filtrate was concentrated at reduced pressure. The residue was purified by HPLC using 10% ethyl acetate-hexane to give 28.7 g (91% yield) of 1-(6-bromohexyl)-3,4-dimethoxybenzene as an oil. The nmr spectrum was consistent with the structure and the low resolution mass spectrum showed the molecular ion at m/z 300 ($C_{14}H_{21}BrO_2$).

EXAMPLE 37

1-(6-Bromohexyl)-3,4-bis-(phenylmethoxy)benzene

Boron tribromide (66 mL, 0.066 mol, 1M in methylene chloride) was added dropwise over 15 minutes to a cooled (−70°) solution of 10 g (0.033 mol) of 1-(6-bromohexyl)-3,4-dimethoxybenzene benezenl in 200 mL of methylene chloride which was stirred in an argon atmosphere. The reaction mixture was stirred at −70° for 30 minutes and at 23° for 3 hours. After cooling in an ice bath, 40 mL of water 20 mL of 3N hydrochloric acid were added and the mixture was stirred at 23° for 1 hour. The organic layer was separated, dried and concentrated at reduced pressure to an oil which was crystallized from chloroform-hexane to give 8.3 g (92% yield), mp 60°–62°, of 1(6-bromohexyl)-3,4-dihydroxybenzene.

Anal. Calcd. for $C_{12}H_{17}BrO_2$: C, 52.76; H, 6.27; Br, 29.25. Found: C, 52.66; H, 6.17; H, 29.46.

A mixture of 8.3 g (0.030 mol) of 1-(6-bromohexyl)-3,4-dihydroxybenzene, 18 mL (0.15 mol) of benzyl bromide and 13 g (0.09 mol) of potassium carbonate in 160 mL of acetone-50 mL of dimethylformamide was stirred at reflux for 24 hours. Potassium carbonate (4 g) was added and stirring at reflux was continued for 48 hours. The reaction mixture was cooled, filtered and the filtrate was concentrated at reduced pressure to an oil. Purification by HPLC using 1% ethyl acetate-hexane gave 6.4 g (47% yield) of 1-(6-bromohexyl)-3,4-bis-(phenylmethoxy)benzene. The nmr spectrum was consistent with the structure and the low resolution mass spectrum showed the molecular ion at m/z 452 ($C_{26}H_{29}BrO_2$).

EXAMPLE 38

(S)-alpha-methyl-6-[6-[3 4-bis(phenylmethoxy)phenyl]hexyloxy]-2-naphthaleneacetic acid ethyl ester A mixture of 2.2 g (4.86 mmol) of 1-(6-bromohexyl)-3,4-bis(phenylmethoxy)benzene, 1.0 g (4.1 mmol) of (S)-alpha-methyl-6-hydroxy-2-naphthaleneacetic acid ethyl ester, 0.68 g (4.5 mmol) sodium iodide and 2.4 g (17.4 mmol) of potassium carbonate in 50 mL of acetone-50 mL of dimethylformamide was stirred at reflux for 23 hours. The reaction mixture was filtered and the filtrate was concentrated at reduced pressure. The residue was purified by HPLC using 10% ethyl acetate-hexane to give 2.2 g (87% yield) of (S)-alpha-methyl-6-[6-[3,4-bis(phenylmethoxy)-phenyl]hexyloxy]-2-naphthaleneacetic acid ethyl ester as an oil. The nmr was consistent with the structure.

EXAMPLE 39

(S)-alpha-Methyl-6-[6-[3,4-bis(phenylmethoxy]phenyl]-hexyloxy]-2-naphthaleneacetic acid A mixture of 2.2 g (3.6mmol) of (S)-alpha-methyl-6-[6-[3,4bis-(phenylmethoxy)phenyl]hexyloxy]-2-naphthaleneacetic acid ethyl ester and 17 mL (17 mmol) of 1N sodium hydroxide in 50 mL of methanol- 17 mL of dioxane was stirred at reflux for 6 hours. Methanol (100 mL) and 1.2 mL (7.6 mmol) of 6N sodium hydroxide were added and the mixture was stirred at reflux for 7 hours. The solvents were removed under reduced pressure, the residue was acidified and the product was extracted with ethyl acetate. The dried extract was concentrated to an oil which was crystallized from ether-hexane to give 1.25 g (59% yield), mp 80°–82°, of (S)-alpha-methyl-6-[6-[3,4-bis(phenylmethoxy)-phenyl]-hexyloxy]-2-naphthaleneacetic acid.

Anal. Calcd. for $C_{39}H_{40}O_5$: C, 79.56; H, 6.85, Found: C, 79.34; H, 6.78.

EXAMPLE 40

(S)-6-[6-(3,4-Dihydroxyphenyl)hexyloxy)-alpha-methyl-2-naphthaleneacetic acid

A mixture of 1.2 g of (S)-alpha-methyl-6-[6-[3,4-bis-(phenylmethoxy)phenyl]hexyloxy]-2-naphthaleneacetic acid and 0.2 g of 01% palladium on carbon in 35 mL of ethyl acetate- 5 mL of tetrahydrofuran was stirred in a hydrogen atmosphere for 18 hours. The reaction mixture was filtered through a Celite pad and the filtrate was concentrated under reduced pressure. The residue was crystallized from ethyl acetate-hexane to give 0.86 g (95% yield), mp 103°–106°; of (S)-6-[6-(3,4-dihydroxyphenyl)hexyloxy]-alpha-methyl-2-naphthaleneacetic acid.

Anal. Calcd for $C_{25}H_{28}O_5$: C, 73.51; H, 6.91. Found: C, 73.42; H, 6.93.

EXAMPLE 41

TABLET FORMULATION (Wet Granulation)

| Item | Ingredient | mg/tablet | | |
|---|---|---|---|---|
| | | 100 mg | 500 mg | 1000 mg |
| 1. | (S)-6-[6-(2,3-dihydroxy-phenyl)hexyloxy]-α-methyl-2-naphthalene acetic acid | 100 | 500 | 1000 |
| 2. | Lactose | 132 | — | — |
| 3. | Pregelatinized Starch | 16 | 30 | 50 |
| 4. | Modified Starch | 30 | 40 | 50 |
| 5. | Magnesium Stearate | 2 | 6 | 8 |
| | Total | 280 | 576 | 1108 |

Manufacturing Procedure:

1 Mix items 1, 2, 3 and 4 and granulate with water.
2. Dry the granulation at 50° C.
3. Pass the granulation through suitable milling equipment.
4. Add item 5 and mix for three minutes; compress on a suitable press.

EXAMPLE 42

CAPSULE FORMULATION

| Ingredients | mg/capsule | | | |
|---|---|---|---|---|
| 1. (S)-6-[6-(2,3-dihydroxy-phenyl)hexyloxy]-α-methyl-2-naphthalene acetic acid | 25 | 50 | 100 | 500 |
| 2. Lactose Hydrous | 143 | 168 | 148 | — |
| 3. Corn Starch | 20 | 20 | 40 | 70 |
| 4. Talc | 10 | 10 | 10 | 25 |
| 5. Magnesium Stearate | 2 | 2 | 2 | 5 |
| Total | 200 | 250 | 300 | 600 |

Manufacturing Procedure:

1. Mix items 1, 2 and 3 in a suitable mixer for 30 minutes.
2. Add items 4 and 5 and mix for 3 minutes
3. Fill into suitable capsules.

EXAMPLE 43

WET GRANULATION FORMULATION

| | Ingredients | mg/tablet | |
|---|---|---|---|
| 1. | (S)-6-[6-2,3-dihydroxy-phenyl)hexyloxy]-60-methyl-2-naphthalene acetic acid | 25 | 50 |
| 2. | Polyvinyl Pyrrolidone | 5 | 10 |
| 3. | Lactose Anhydrous DTG | 133 | 142 |
| 4. | Avicel PH 102 | 25 | 30 |
| 5. | Modified Starch | 10 | 15 |
| 6. | Magnesium Stearate | 2 | 3 |
| | Total | 200 | 250 |

Manufacturing Procedure:

1. Dissolve item 2 in water.
2. Mix items 1, 3, 4 and 5 in a suitable mixer and granulate with solution in Step 1.
3. Dry overnight at 45° C., screen through #20 mesh, and add item 6 and mix. Compress on a suitable press.

EXAMPLE 44

SOFT GELATIN CAPSULE FORMULATION

| | Ingredients | mg/capsule | |
|---|---|---|---|
| 1. | (S)-6-[6-(2,3-dihydroxyphenyl)-hexyloxy]-α-methyl-2-naphthalene acetic acid | 50 | 250 |
| 2. | PEG 400 | 325 | 550 |
| 3. | MCM 90 | 100 | 150 |
| 4. | Tween 80 | 25 | 50 |
| | Total | 500 | 1000 |

Manufacturing Procedure:

1. Dissolve item 1 in item 2.
2. Add item 3 and mix well.
3. Add item 4 and mix well until dissolved.
4. Fill in soft gelatin capsules.

EXAMPLE 45

CREAM 5%

| | Ingredients | g/kg | Reasonable Variations |
|---|---|---|---|
| 1. | (S)-6-[6-(2,3-dihydroxy-phenyl)hexyloxy]-α-methyl-2-naphthalene acetic acid | 51.50* | — |
| 2. | Glyceryl Monostearate S.E.[1] | 100.00 | 80–120 |
| 3. | Polysorbate 60[2] | 20.00 | 15–25 |
| 4. | Cetyl Alcohol | 50.00 | 40–60 |
| 5. | Petrolatum | 70.00 | 50–90 |
| 6. | Methylparaben | 1.50 | 1.25–1.75 |
| 7. | Propylparaben | 0.50 | 0.4–0.6 |
| 8. | Propylene Glycol | 200.00 | 150–250 |
| 9. | Purified Water | 521.70 | 475–575 |
| | Total | 1015.20 | |

*3% excess
[1] Arlacel 165
[2] Tween 60

Manufacturing Procedure:

1. Melt items 2, 3, 4 and 5 by heating to 80° C.
2. In a separate container, dissolve items 6 and 7 in item 9 at 80° C.
3. Dissolve item 1 in item 8 at 80° C. and add to step 2.

4. Add step 1 at 80° C. and mix vigorously. Cool slowly to RT.

EXAMPLE 46

SUPPOSITORY

| Ingredients | g/suppository | | | |
|---|---|---|---|---|
| 1. (S)-6-[6-(2,3-dihydroxy-phenyl)hexyloxy]-α-methyl-2-naphthalene acetic acid | .025 | 0.10 | 0.50 | 1.00 |
| 2. Witepsol H15 | 1.975 | 1.90 | 1.50 | 1.00 |
| Total | 2.000 | 2.00 | 2.00 | 2.00 |

Manufacturing Procedure:

1. Melt item 2 at 50°–55° C.
2. Add item 1 to Step 1 with mixing until dissolved or uniformly distributed.
3. Fill Step 2 into suitable suppository molds at 50° C. Alloy to cool and congeal. Refrigerate for several hours. EXAMPLE 47

ENEMA

| Ingredients | mg/5 mL | | |
|---|---|---|---|
| 1. (S)-6-[6-(2,3-dihydroxy-phenyl)hexyloxy]-α-methyl-2-naphthalene acetic acid | 25 | 100 | 500 |
| 2. Propylene Glycol | 1500 | 1500 | 1500 |
| 3. Methylparaben | 4 | 4 | 4 |
| 4. Propylparaben | 1 | 1 | 1 |
| 5. Purified Water q.s. | 5 mL | 5 mL | 5 mL |

Manufacturing Procedure:

1. Dissolve items 3 and 4 in item 5 at 80° C. Cool to 50° C.
2. Dissolve item 1 in item 2 and add to Step 1.
3. Cool to room temperature.

We claim:

1. A compound of the formula

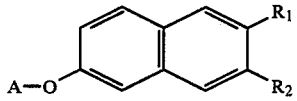
I wherein one of $R_1$ and $R_2$ is

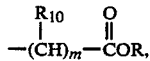

and the other is hydrogen, wherein R is hydrogen or lower alkyl, $R_{10}$ is hydrogen or lower alkyl, and m is 0 or 1, A is

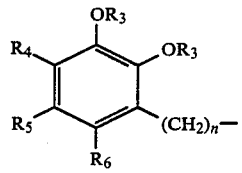
A' wherein $R_3$ is hydrogen or acyl, $R_4$ is hydrogen, halogen, lower alkyl, aryl or cycloalkyl, $R_5$ and $R_6$ independently are hydrogen or halogen, and n is an integer from 2–10, or A is

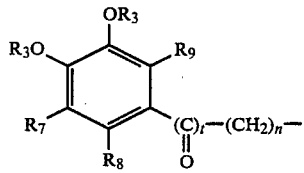
A″ wherein $R_3$ is hydrogen or acyl, $R_7$ is hydrogen or lower alkyl, $R_8$ and $R_9$, independently, are hydrogen, lower alkyl or halogen, t is 0 or 1, and n is an integer from 2–10, and, when $R_{10}$ is lower alkyl, an enantiomer or racemate thereof, and, when R is hydrogen, a salt thereof with a pharmaceutically acceptable base.

2. A compound, in accordance with claim 1, of the formula

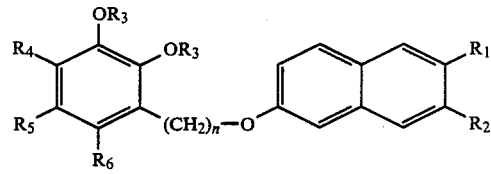
Ia wherein one of $R_1$ and $R_2$ is

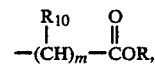

and the other is hydrogen, wherein R is hydrogen or lower alkyl, $R_{10}$ is hydrogen or lower alkyl, and m is 0 or 1, R is hydrogen or acyl, $R_4$ is hydrogen, halogen, lower alkyl, aryl or cycloalkyl, R and $R_6$ independently are hydrogen or halogen, and n is an integer from 2–10, and, when $R_{10}$ is lower alkyl, an enantiomer or racemate thereof, and, when R is hydrogen, a salt thereof with a Pharmaceutically acceptable base.

3. A compound, in accordance with claim 1, of the formula

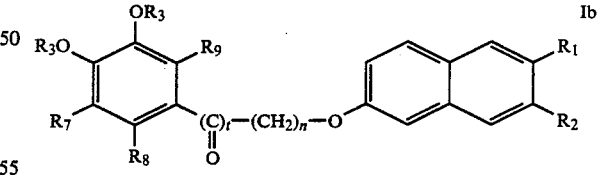
Ib wherein one of $R_1$ and $R_2$ is

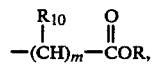

and the other is hydrogen, wherein R is hydrogen- or lower alkyl, $R_{10}$ is hydrogen or lower alkyl, and m is 0 or 1, $R_3$ is hydrogen or acyl, $R_7$ is hydrogen or lower alkyl, $R_8$ and $R_9$ independently, are hydrogen, lower alkyl or halogen, t is 0 or 1, and n is an integer from 2–10, and, when R₁₀ is lower alkyl, an enantiomer or racemate thereof, and, when R is hydrogen, a salt thereof with a pharmaceutically acceptable base.

4. A compound, in accordance with claim 2, wherein R₁ is

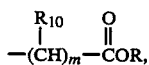

R₂ is hydrogen, R₁₀ is hydrogen or methyl, and R₃ is hydrogen.

5. A compound, in accordance with claim 2, wherein R₁ is

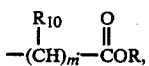

R₂ is hydrogen, R₁₀ is hydrogen or methyl, R₃ is hydrogen, R₄ is hydrogen, halogen or lower alkyl, and n is an integer from 4 to 8.

6. A compound, in accordance with claim 3, wherein R₁ is

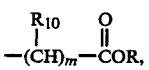

R₁₀ is hydrogen or methyl, and R₃ is hydrogen.

7. A compound, in accordance with claim 3, wherein R₁ is

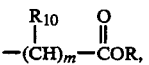

R₂ is hydrogen, R₁₀ is hydrogen or methyl, R₃ is hydrogen, t is 0, n is an integer from 4–8, R₇ and R₉ independently, are hydrogen or lower alkyl, and R₈ is hydrogen.

8. A compound in accordance with claim 1, (S)-6-[6-(2,3-dihydroxyphenyl)hexyloxy]-alpha-methyl-2-naphthaleneacetic acid.

9. A compound, in accordance with claim 1, (S)-6-[6-(2,3-dihydroxyphenyl)hexyloxy]-alpha-methyl-2-naphthaleneacetic acid ethyl ester.

10. A compound, in accordance with claim 1, (Rac)-6-[6-(2,3-dihydroxyphenyl)hexyloxy]-alpha-methyl-2-naphthaleneacetic acid.

11. A compound, in accordance with claim 1, 6-[6-(2,3-dihydroxyphenyl)hexyloxy]-2-naphthaleneacetic acid.

12. A compound, in accordance with claim 1, 6-[6-(2,3-dihydroxyphenyl)hexyloxy]-2-naphthalenecarboxylic acid.

13. A compound, in accordance with claim 1, (S)-6-[6-(3,4-dihydroxyphenyl)hexyloxy]-alpha-methyl-2-naphthaleneacetic acid.

14. A pharmaceutical composition comprising an effective amount of a compound of the formula

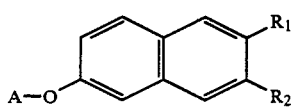

wherein one of R₁ and R₂ is

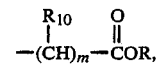

and the other is hydrogen, wherein R is hydrogen or lower alkyl, R₁₀ is hydrogen or lower alkyl, and m is 0 or 1 A is

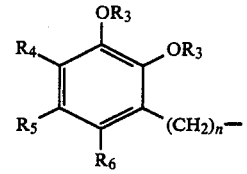

wherein R₃ is hydrogen or acyl, R₄ is hydrogen, halogen, lower alkyl, aryl or cycloalkyl, R₅ and R₆ independently are hydrogen or halogen, and n is an integer from 2–10, or A is

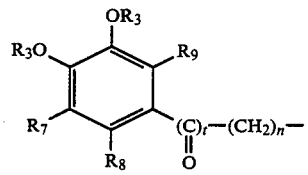

wherein R₃ is hydrogen or acyl, R₇ is hydrogen or lower alkyl, R₈ and R₉, independently, are hydrogen, lower alkyl or halogen, t is 0 or 1, and n is an integer from 2–10, and, when R₁₀ is lower alkyl, an enantiomer or racemate thereof, and, when R is hydrogen, a salt thereof with a pharmaceutically acceptable base, and an inert carrier.

15. A pharmaceutical composition, in accordance with claim 14, which comprises an effective amount of a compound of the formula

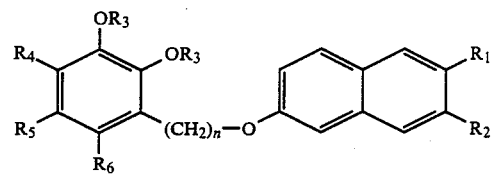

wherein one of R₁ and R₂ is

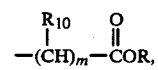

and the other is hydrogen, wherein R is hydrogen or lower alkyl, R₁₀ is hydrogen or lower alkyl, and m is 0 or 1, R₃ is hydrogen or acyl, R₄ is hydrogen, halogen, lower alkyl, aryl or cycloalkyl, R₅ and R₆ independently are hydrogen or halogen, and n is an integer from 2–10, and, when R₁₀ is lower alkyl, an enantiomer or racemate thereof, and, when R is hydrogen, a salt thereof with a pharmaceutically acceptable base, and an inert carrier.

16. A pharmaceutical composition, in accordance with claim 14, which comprises an effective amount of a compound of the formula

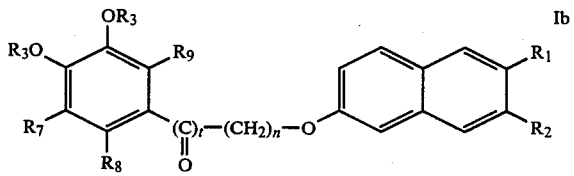

wherein one of $R_1$ and $R_2$ is

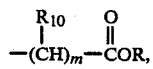

and the other is hydrogen, wherein R is hydrogen or lower alkyl, $R_{10}$ is hydrogen or lower alkyl, and m is 0 or 1, $R_3$ is hydrogen or acyl, $R_7$ is hydrogen or lower alkyl, $R_8$ and $R_9$ independently, are hydrogen, lower alkyl or halogen, t is 0 or 1, and n is an integer from 2–10, and, when $R_{10}$ is lower alkyl, an enantiomer or racemate thereof, and, when R is hydrogen, a salt thereof with a pharmaceutically acceptable base, and an inert carrier.

17. A pharmaceutical composition, in accordance with claim 14, wherein
$R_1$ is

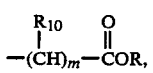

$R_2$ is hydrogen, $R_{10}$ is hydrogen or methyl and $R_3$ is hydrogen.

18. A pharmaceutical composition, in accordance with claim 14, wherein
$R_1$ is

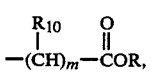

$R_2$ is hydrogen, $R_{10}$ is hydrogen or methyl, $R_3$ is hydrogen, $R_4$ is hydrogen, halogen or lower alkyl, and n is an integer from 4 to 8.

19. A pharmaceutical composition, in accordance with claim 14, wherein the compound of formula I is (S)-6-[6-(2,3-dihydroxyphenyl)hexyloxy]-alpha-methyl-2-naphthaleneacetic acid.

20. A pharmaceutical composition, in accordance with claim 14, wherein the compound of formula I is (S)-6-[6-(2,3-dihydroxyphenyl)hexyloxy]-alpha-methyl-2-naphthaleneacetic acid ethyl ester.

21. A pharmaceutical composition in accordance with claim 14, wherein the compound of formula I is (Rac)-6-[6-(2,3-dihydroxyphenyl)hexyloxy]-alpha-methyl-2-naphthaleneacetic acid.

22. A pharmaceutical composition in accordance with claim 14, wherein the compound of formula I is 6-[6-(2,3-dihydroxyphenyl)hexyloxy]-2-naphthaleneacetic acid.

23. A pharmaceutical composition, in accordance with claim 14, wherein the compound of formula I is 6-[6-(2,3-dihydroxyphenyl)hexyloxy]-2-naphthalenecarboxylic acid.

24. A pharmaceutical composition, in accordance with claim 14, wherein the compound of formula I is (S)-6-[6-(3,4-dihydroxyphenyl)hexyloxy]-alpha-methyl-2-naphthaleneacetic acid.

25. A method of treating inflammatory diseases which comprises administering to a host requiring such treatment an effective amount of a compound of formula

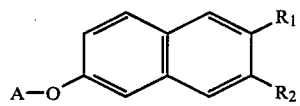

wherein one of $R_1$ and $R_2$ is

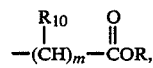

and the other is hydrogen, wherein R is hydrogen or lower alkyl, $R_{10}$ is hydrogen or lower alkyl, and m is 0 or 1 A is

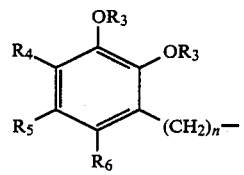

wherein $R_3$ is hydrogen or acyl, $R_4$ is hydrogen, halogen, lower alkyl, aryl or cycloalkyl, $R_5$ and $R_6$ independently are hydrogen or halogen, and n is an integer from 2–10, or A is

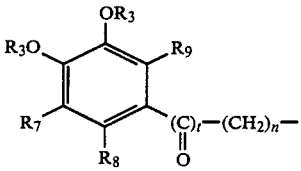

wherein $R_3$ is hydrogen or acyl, $R_7$ is hydrogen or lower alkyl, $R_8$ and $R_9$ independently are hydrogen, lower alkyl or halogen, t is 0 or 1, and n is an integer from 2–10, and, when $R_{10}$ is lower alkyl, an enantiomer or racemate thereof, and, when R is hydrogen, a salt thereof with a pharmaceutically acceptable base.

26. A method, in accordance with claim 25, wherein the compound administered is characterized by the formula

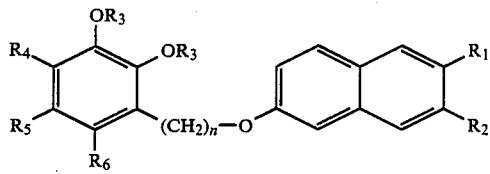

wherein one of $R_1$ and $R_2$ is

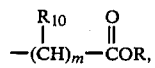

and the other is hydrogen, wherein R is hydrogen or lower alkyl, $R_{10}$ is hydrogen or lower alkyl, and m is 0 or 1, $R_3$ is hydrogen or acyl, $R_4$ is hydrogen, halogen, lower alkyl, aryl or cycloalkyl, R and $R_6$ independently are hydrogen or halogen, and n is an integer from 2-10, when $R_{10}$ is lower alkyl, an enantiomer or racemate thereof, and, when R is hydrogen, a salt thereof with a pharmaceutically acceptable base.

27. A method, in accordance with claim 25, wherein the compound administered is characterized by the formula

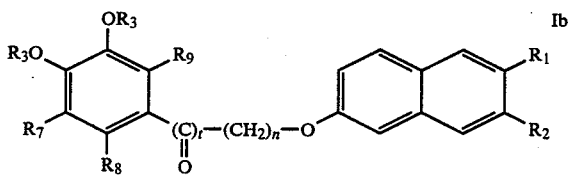

wherein one of $R_1$ and $R_2$ is

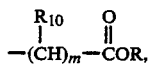

and the other is hydrogen, wherein R is hydrogen or lower alkyl, $R_{10}$ is hydrogen or lower alkyl, and m is 0 or 1, $R_3$ is hydrogen or acyl, $R_7$ is hydrogen or lower alkyl, $R_8$ and $R_9$ independently, are hydrogen, lower alkyl or halogen, t is 0 or 1, and n is an integer from 2-10, and, when $R_{10}$ is lower alkyl, an enantiomer or racemate thereof, and, when R is hydrogen a salt thereof with a pharmaceutically acceptable base.

28. A method, in accordance with claim 25, wherein $R_1$ is

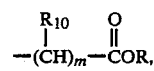

$R_2$ is hydrogen, $R_{10}$ is hydrogen or methyl, and $R_3$ is hydrogen.

29. A method in accordance with claim 25, wherein $R_1$ is

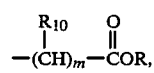

$R_2$ is hydrogen, $R_{10}$ is hydrogen or methyl, $R_3$ is hydrogen, $R_4$ is hydrogen, halogen or lower alkyl, and n is an integer from 4 to 8.

* * * * *

UNITED STATES PATENT AND TRADEMARK OFFICE
CERTIFICATE OF CORRECTION

PATENT NO. : 4,937,373
DATED : June 26, 1990
INVENTOR(S) : Matthew Carson, Ru-Jen Lee Han, Ronald Andrew LaMahieu It is certified that error appears in the above-identified patent and that said Letters Patent is hereby corrected as shown below:

Claim 2, Column 32, Line 39

"R" should be -- $R_3$ --,

Claim 2, Column 32, Line 40

"R" should be -- $R_5$ --,

Claim 26, Column 37, Line 4

"R" should be -- $R_5$ --,

Signed and Sealed this

Seventeenth Day of September, 1991

*Attest:*

HARRY F. MANBECK, JR.

*Attesting Officer*    *Commissioner of Patents and Trademarks*